US008222049B2

(12) United States Patent
Linder et al.

(10) Patent No.: US 8,222,049 B2
(45) Date of Patent: Jul. 17, 2012

(54) FLOW CONTROL IN MICROFLUIDIC SYSTEMS

(75) Inventors: Vincent Linder, Wilmington, MA (US); David Steinmiller, Cambridge, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 396 days.

(21) Appl. No.: 12/428,372

(22) Filed: Apr. 22, 2009

(65) Prior Publication Data

US 2009/0266421 A1 Oct. 29, 2009

Related U.S. Application Data

(60) Provisional application No. 61/047,923, filed on Apr. 25, 2008.

(51) Int. Cl.
*G01N 33/536* (2006.01)

(52) U.S. Cl. ....... 436/536; 435/7.92; 435/174; 435/338; 435/286.5

(58) Field of Classification Search ........................ None
See application file for complete search history.

(56) References Cited

U.S. PATENT DOCUMENTS 3,735,640 A 5/1973 Chizhov et al.
4,318,994 A 3/1982 Meyer et al.
4,963,498 A 10/1990 Hillman et al.
5,051,237 A 9/1991 Grenner et al.
5,219,762 A 6/1993 Katamine et al.
5,286,454 A 2/1994 Nilsson et al.

(Continued)

FOREIGN PATENT DOCUMENTS

EP 0 110 771 B1 3/1988

(Continued)

OTHER PUBLICATIONS

International Search Report and Written Opinion for PCT/US2008/005577 mailed Apr. 3, 2009.

(Continued)

*Primary Examiner* — N. C. Yang
(74) *Attorney, Agent, or Firm* — Wolf, Greenfield & Sacks, P.C.

(57) ABSTRACT

Microfluidic systems and methods including those that provide control of fluid flow are provided. Such systems and methods can be used, for example, to control pressure-driven flow based on the influence of channel geometry and the viscosity of one or more fluids inside the system. One method includes flowing a plug of a low viscosity fluid and a plug of a high viscosity fluid in a channel including a flow constriction region and a non-constriction region. In one embodiment, the low viscosity fluid flows at a first flow rate in the channel and the flow rate is not substantially affected by the flow constriction region. When the high viscosity fluid flows from the non-constriction region to the flow constriction region, the flow rates of the fluids decrease substantially, since the flow rates, in some systems, are influenced by the highest viscosity fluid flowing in the smallest cross-sectional area of the system (e.g., the flow constriction region). This causes the fluids to flow at the same flow rate at which the high viscosity fluid flows in the flow constriction region. Accordingly, by designing microfluidic systems with flow constriction regions positioned at particular locations and by choosing appropriate viscosities of fluids, a fluid can be made to speed up or slow down at different locations within the system without the use of valves and/or without external control.

35 Claims, 13 Drawing Sheets

U.S. PATENT DOCUMENTS

| | | | |
|---|---|---|---|
| 5,376,252 A | 12/1994 | Ekström et al. | |
| 5,478,751 A | 12/1995 | Oosta et al. | |
| 5,486,335 A | 1/1996 | Wilding et al. | |
| 5,571,410 A | 11/1996 | Swedberg et al. | |
| 5,635,358 A | 6/1997 | Wilding et al. | |
| 5,637,469 A | 6/1997 | Wilding et al. | |
| 5,726,026 A | 3/1998 | Wilding et al. | |
| 5,731,212 A | 3/1998 | Gavin et al. | |
| 5,842,787 A | 12/1998 | Kopf-Sill et al. | |
| 5,866,345 A | 2/1999 | Wilding et al. | |
| 5,869,004 A | 2/1999 | Parce et al. | |
| 5,876,675 A | 3/1999 | Kennedy | |
| 5,942,443 A | 8/1999 | Parce et al. | |
| 5,955,028 A | 9/1999 | Chow | |
| 5,957,579 A | 9/1999 | Kopf-Sill et al. | |
| 5,976,336 A | 11/1999 | Dubrow et al. | |
| 6,042,709 A | 3/2000 | Parce et al. | |
| 6,046,056 A | 4/2000 | Parce et al. | |
| 6,103,199 A | 8/2000 | Bjornson et al. | |
| 6,136,272 A | 10/2000 | Weigl et al. | |
| 6,146,489 A | 11/2000 | Wirth | |
| 6,146,589 A | 11/2000 | Chandler | |
| 6,168,948 B1 | 1/2001 | Anderson et al. | |
| 6,176,962 B1 | 1/2001 | Soane et al. | |
| 6,184,029 B1 | 2/2001 | Wilding et al. | |
| 6,186,660 B1 | 2/2001 | Kopf-Sill et al. | |
| 6,214,560 B1 | 4/2001 | Yguerabide et al. | |
| 6,238,538 B1 | 5/2001 | Parce et al. | |
| 6,241,560 B1 | 6/2001 | Furusawa et al. | |
| 6,251,343 B1 | 6/2001 | Dubrow et al. | |
| 6,274,337 B1 | 8/2001 | Parce et al. | |
| 6,296,020 B1 | 10/2001 | McNeely et al. | |
| 6,333,200 B1 | 12/2001 | Kaler et al. | |
| 6,361,958 B1 | 3/2002 | Shieh et al. | |
| 6,413,782 B1 | 7/2002 | Parce et al. | |
| 6,416,642 B1 | 7/2002 | Alajoki et al. | |
| 6,429,025 B1 | 8/2002 | Parce et al. | |
| 6,432,720 B2 | 8/2002 | Chow | |
| 6,479,299 B1 | 11/2002 | Parce et al. | |
| 6,488,872 B1 | 12/2002 | Beebe et al. | |
| 6,488,894 B1 | 12/2002 | Miethe et al. | |
| 6,488,896 B2 | 12/2002 | Weigl et al. | |
| 6,551,841 B1 | 4/2003 | Wilding et al. | |
| 6,613,512 B1 | 9/2003 | Kopf-Sill et al. | |
| 6,613,525 B2 | 9/2003 | Nelson et al. | |
| 6,620,625 B2 | 9/2003 | Wolk et al. | |
| 6,632,619 B1 | 10/2003 | Harrison et al. | |
| 6,638,482 B1 | 10/2003 | Ackley et al. | |
| 6,656,430 B2 | 12/2003 | Sheppard, Jr. et al. | |
| 6,669,831 B2 | 12/2003 | Chow et al. | |
| 6,709,869 B2 | 3/2004 | Mian et al. | |
| 6,716,620 B2 | 4/2004 | Bashir et al. | |
| 6,742,661 B1 | 6/2004 | Schulte et al. | |
| 6,761,962 B2 | 7/2004 | Bentsen et al. | |
| 6,780,584 B1 | 8/2004 | Edman et al. | |
| 6,794,197 B1 | 9/2004 | Indermuhle et al. | |
| 6,818,184 B2 | 11/2004 | Fulwyler et al. | |
| 6,827,095 B2 | 12/2004 | O'Connor et al. | |
| 6,828,143 B1 | 12/2004 | Bard | |
| 6,830,936 B2 | 12/2004 | Anderson et al. | |
| 6,858,185 B1 | 2/2005 | Kopf-Sill et al. | |
| 6,878,271 B2 | 4/2005 | Gilbert et al. | |
| 6,878,755 B2 | 4/2005 | Singh et al. | |
| 6,949,377 B2 | 9/2005 | Ho | |
| 6,953,550 B2 | 10/2005 | Sheppard, Jr. et al. | |
| 6,989,128 B2 | 1/2006 | Alajoki et al. | |
| 7,005,292 B2 | 2/2006 | Wilding et al. | |
| 7,015,046 B2 | 3/2006 | Wohlstadter et al. | |
| 7,018,830 B2 | 3/2006 | Wilding et al. | |
| 7,067,263 B2 | 6/2006 | Parce et al. | |
| 7,087,148 B1 | 8/2006 | Blackburn et al. | |
| 7,091,048 B2 | 8/2006 | Parce et al. | |
| 2002/0019059 A1 | 2/2002 | Chow et al. | |
| 2002/0142618 A1* | 10/2002 | Parce et al. | 438/751 |
| 2002/0149369 A1* | 10/2002 | Peck et al. | 324/321 |
| 2003/0012697 A1 | 1/2003 | Hahn et al. | |
| 2003/0082081 A1 | 5/2003 | Yves et al. | |
| 2003/0118486 A1 | 6/2003 | Zhou et al. | |
| 2003/0138969 A1* | 7/2003 | Jakobsen et al. | 436/180 |
| 2003/0152927 A1 | 8/2003 | Jakobsen et al. | |
| 2003/0207328 A1 | 11/2003 | Yguerabide et al. | |
| 2004/0077074 A1 | 4/2004 | Ackley et al. | |
| 2004/0115094 A1 | 6/2004 | Gumbrecht et al. | |
| 2004/0228771 A1 | 11/2004 | Zhou et al. | |
| 2004/0241693 A1 | 12/2004 | Ricoul et al. | |
| 2005/0118073 A1 | 6/2005 | Facer et al. | |
| 2005/0161669 A1 | 7/2005 | Jovanovich et al. | |
| 2005/0221281 A1 | 10/2005 | Ho | |
| 2005/0238545 A1 | 10/2005 | Parce et al. | |
| 2005/0255003 A1 | 11/2005 | Summersgill et al. | |
| 2006/0002827 A1 | 1/2006 | Curcio et al. | |
| 2006/0094119 A1 | 5/2006 | Ismagilov et al. | |
| 2006/0257992 A1 | 11/2006 | McDevitt et al. | |
| 2006/0275852 A1 | 12/2006 | Montagu | |
| 2007/0119510 A1* | 5/2007 | Kartalov et al. | 137/825 |
| 2008/0085219 A1 | 4/2008 | Beebe et al. | |
| 2010/0137163 A1* | 6/2010 | Link et al. | 506/16 |
| 2010/0267013 A1* | 10/2010 | Su et al. | 435/6 |

FOREIGN PATENT DOCUMENTS

| | | |
|---|---|---|
| EP | 0 643 307 A1 | 3/1995 |
| EP | 1 054 259 A1 | 11/2000 |
| WO | WO 91/01003 A | 1/1991 |
| WO | WO 02/22250 A2 | 3/2002 |
| WO | WO 03/054513 A2 | 7/2003 |
| WO | WO 2004/087951 A3 | 10/2004 |
| WO | WO 2005056186 A1 | 6/2005 |
| WO | WO 2006018044 A1 | 2/2006 |
| WO | WO 2006/056787 A1 | 6/2006 |
| WO | WO 2006113727 A2 | 10/2006 |
| WO | WO 2007/081387 A | 7/2007 |

OTHER PUBLICATIONS

International Search Report and Written Opinion for PCT/US2009/002496, mailed Jul. 24, 2009.

Ahn, C. et al., "Disposable Smart Lab on a Chip for Point-of-Care Clinical Diagnostics", *Proceedings of the IEEE*, vol. 92, No. 1, pp. 154-173 (2004).

Andersson, et al., "Micromachined flow-through filter-chamber for chemical reactions on beads", *Sensors and Actuators*, vol. B67, pp. 203-208 (2000).

Atencia, J et al., "Capillary inserts in microcirculatory systems", *Lab Chip*, 6, 575-577 (2006).

Atencia, J. et al. "Steady flow generation in microcirculatory systems", *Lab Chip*, 6, 567-574 (2006).

Darion, et al., "Chemical sensing using an integrated microfluidic system based on the Berthelot reaction", *Sensors and Actuators B*, vol. 76, pp. 235-243 (2001).

Dodge, et al., "Electrokinetically Driven Microfluidic Chips with Surface-Modified Chambers for Heterogeneous Immunoassays", *Anal. Chem.*, vol. 73, pp. 3400-3409 (2001).

Fredrickson, C. et al., "Macro-to-micro interfaces for microfluidic devices", *Lab Chip*, 4, 526-533 (2004).

Grodzinski, P. et al., "A Modular Microfluidic System for Cell Preconcentration and Genetic Sample Preparation", *Biomedical Microdevices*, 5:4,303-310 (2003).

Juncker, et al., "Autonomous Microfluidic Capillary Systems", *Anal. Chem*, vol. 74, pp. 6139-6144 (2002).

Linder, et al., "Reagent-Loaded Cartridges for Valveless and Automated Fluid Delivery in Microfluidic Devices", *Anal Chem.*, vol. 77, No. 1, pp. 64-71 (2005).

Moorthy, et al., "Microfluidic tectonics platform: a colorimetric, disposable botulinum toxin enzyme-linked immunosorbent assay system", *Electrophoresis*, vol. 25, pp. 1705-1713 (2004).

Obeid, et al., "Microfabricated Device for DNA and RNA Amplification by Continuous-Flow Polymerase Chain Reaction and Reverse Transcription-Polymerase Chain Reaction with Cycle Number Selection", *Anal. Chem.*, vol. 75, pp. 288-295 (2003).

Sia, S., et al., "An Integrated Approach to a Portable and Low-Cost Immunoassay for Resource-Poor Settings",*Angew. Chem. Int. Ed.*, vol. 43, pp. 498-502 (2004).

Sia, S., et al., “Microfluidic devices fabricated in poly(dimethlysiloxane) for biological studies”, *Electrophoresis*, vol. 24, pp. 3563-3576 (2003).
Song et al., “A microfluidic system for controlling reaction networks in time”, *Angew. Chem. Int. Ed.*, vol. 42, No. 7, 768-772 (2003).
Weigle, et al., “Lab-on-a-chip for drug development”, *Advanced Drug Delivery Reviews*, vol. 55, pp. 349-377 (2003).
Proceedings of uTAS 2004, 8th International Conference on Miniaturized Systems in Chemistry and Life Sciences, Sep. 26-30, Malmo, Sweden, Edited by Thomas Laurell, Johan Nilsson, Klays Jensen, D. Jed Harrison, Jorg P. Kutter, The Royal Society of Chemistry, pp. 1-135 (2004).

* cited by examiner

FLOW CONTROL IN MICROFLUIDIC SYSTEMS

RELATED APPLICATIONS

This application claims the benefit of U.S. Provisional Patent Application Ser. No. 61/047,923, filed Apr. 25, 2008, entitled "FLOW CONTROL IN MICROFLUIDIC SYSTEMS," by Linder, et al., which is incorporated herein by reference in its entirety for all purposes.

FIELD OF INVENTION

The present invention relates generally to microfluidic systems, and more specifically, to microfluidic systems and methods that provide control of fluid flow.

BACKGROUND

The manipulation of fluids plays an important role in fields such as chemistry, microbiology and biochemistry. These fluids may include liquids or gases and may provide reagents, solvents, reactants, or rinses to chemical or biological processes. While various microfluidic methods and devices, such as microfluidic assays, can provide inexpensive, sensitive and accurate analytical platforms, fluid manipulations—such as sample introduction, introduction of reagents, storage of reagents, separation of fluids, modulation of flow rate, collection of waste, extraction of fluids for off-chip analysis, and transfer of fluids from one chip to the next—can add a level of cost and sophistication. Accordingly, advances in the field that could reduce costs, simplify use, and/or improve fluid manipulations in microfluidic systems would be beneficial.

SUMMARY OF THE INVENTION

Microfluidic systems that provide control of fluid flow and methods associated therewith are provided.

In one aspect of the invention, a series of methods are provided. In one embodiment, a method comprises flowing a first fluid from a first channel portion to a second channel portion in a microfluidic system, wherein a fluid path defined by the first channel portion has a larger cross-sectional area than a cross-sectional area of a fluid path defined by the second channel portion. The method also includes flowing a second fluid in a third channel portion in the microfluidic system in fluid communication with the first and second channel portions, wherein the viscosity of the first fluid is different than the viscosity of the second fluid, and wherein the first and second fluids are substantially incompressible. Without stopping the first or second fluids, the method includes causing a volumetric flow rate of the first and second fluids to decrease by a factor of at least 3 in the microfluidic system as a result of the first fluid flowing from the first channel portion to the second channel portion, compared to the absence of flowing the first fluid from the first channel portion to the second channel portion. The method also includes effecting a chemical and/or biological interaction involving a component of the first or second fluids at a first analysis region in fluid communication with the channel portions while the first and second fluids are flowing at the decreased flow rate.

In another embodiment, a method comprises flowing a first fluid from a first channel portion to a second channel portion in a microfluidic system, wherein a fluid path defined by the first channel portion has a larger cross-sectional area than a cross-sectional area of a fluid path defined by the second channel portion. A second fluid is flowed in a third channel portion in the microfluidic system in fluid communication with the first and second channel portions, wherein the viscosity of the first fluid is different than the viscosity of the second fluid, and wherein the first and second fluids are substantially incompressible. Without stopping the first or second fluids, the method includes causing a volumetric flow rate of the first and second fluids to decrease by a factor of at least 50 in the microfluidic system as a result of the first fluid flowing from the first channel portion to the second channel portion, compared to the absence of flowing the first fluid from the first channel portion to the second channel portion.

In another embodiment, a method comprises applying a substantially constant, non-zero pressure drop across an inlet and an outlet of a microfluidic system comprising a microfluidic channel in fluid communication with a first analysis region, while carrying out the following steps: flowing, at a first volumetric flow rate, a first fluid and a second fluid in a microfluidic channel positioned between the inlet and the outlet and in fluid communication with the first analysis region; without changing a cross-sectional area of a channel of the microfluidic system and without stopping the first or second fluids, causing at least a portion of the first fluid and/or second fluid to flow at a second volumetric flow rate in at least a portion of the first analysis region, wherein the second volumetric flow rate differs from the first volumetric flow rate by a factor of at least 3; and effecting a chemical and/or biological interaction involving a first component of the first or second fluids at the first analysis region at the slower of the first and second volumetric flow rates.

In another embodiment, a method of operating a microfluidic system comprises applying a pressure drop across an inlet and an outlet of a microfluidic system, while carrying out the following steps: flowing a first fluid from a first channel portion to a second channel portion positioned between the inlet and the outlet of the microfluidic system, wherein a fluid path defined by the first channel portion has a larger cross-sectional area than a cross-sectional area of a fluid path defined by the second channel portion; without stopping the first fluid, causing a volumetric flow rate of the first fluid to decrease by a factor of at least 50 in the microfluidic system as a result of the first fluid flowing from the first channel portion to the second channel portion; and preventing any of the first fluid from exiting the microfluidic system via the outlet during operation of the microfluidic system as a result of the decrease in volumetric flow rate of the first fluid.

In another aspect of the invention, a kit is provided. The kit comprises a microfluidic system comprising an inlet, an outlet, and a microfluidic channel positioned between the inlet and the outlet. The microfluidic channel comprises a first channel portion comprising a fluid path having a first cross-sectional area and a second channel portion comprising a fluid path having a second cross-sectional area positioned immediately adjacent the first channel portion, wherein the first cross-sectional area is greater than the second cross-sectional area. The microfluidic system also includes a first analysis region in fluid communication with the second channel portion and positioned between the inlet and the outlet. The kit further includes a known volume of a first fluid to be flowed in the microfluidic system, and a known volume of a second fluid to be flowed in the microfluidic system, the second fluid having a viscosity such that an act of flowing the second fluid from the first channel portion to the second channel portion results in a decrease in volumetric flow rate of the first fluid by a factor of at least 50 compared to the flowing of the first fluid from the first channel portion to the second channel portion. The volume and viscosity of the second fluid and the dimensions of the first and second channel portions are determined to allow the first fluid to flow for a known, pre-calculated amount of time in the analysis region during use.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1A:
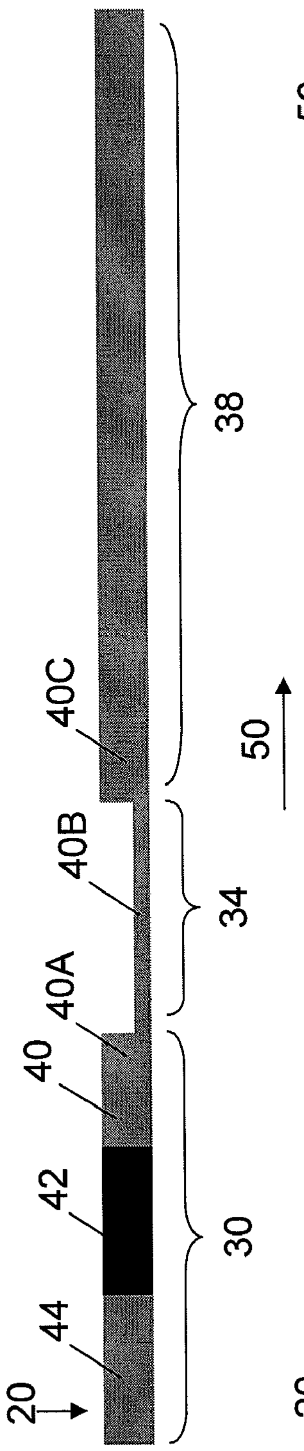
FIGS. 1A-1H show various microfluidic channels including flow constriction regions that can be used to control fluid flow in a microfluidic system according to one embodiment of the invention.

Microfluidic systems and methods including those that provide control of fluid flow are provided. Such systems and methods can be used, for example, to control pressure-driven flow based on the influence of channel geometry and the viscosity of one or more fluids inside the system. One method includes flowing a plug of a low viscosity fluid and a plug of a high viscosity fluid in a channel including a flow constriction region and a non-constriction region. In one embodiment, the low viscosity fluid flows at a first flow rate in the channel and the flow rate is not substantially affected by the fluid flowing in the flow constriction region. When the high viscosity fluid flows from the non-constriction region to the flow constriction region, the flow rates of the fluids decrease substantially, since the flow rates, in some systems, are influenced by the highest viscosity fluid flowing in the smallest cross-sectional area of the system (e.g., the flow constriction region). This causes the low viscosity fluid to flow at a second, slower flow rate than its original flow rate, e.g., at the same flow rate at which the high viscosity fluid flows in the flow constriction region. Accordingly, by designing microfluidic systems with flow constriction regions positioned at particular locations and by choosing appropriate viscosities of fluids, a fluid can be made to speed up or slow down at different locations within the system without the use of valves and/or without external control. In addition, as described in more detail below, the length of the channel portions can be chosen to allow a fluid to remain in a particular area of the system for a certain period of time. Such systems are particularly useful for performing chemical and/or biological assays, as well as other applications in which timing of reagents is important.

The articles, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. patent application Ser. No. 12/113,503, filed May 1, 2008 and entitled "Fluidic Connectors and Microfluidic Systems"; U.S. patent application Ser. No. 12/196,392, filed Aug. 22, 2008, entitled "Liquid containment for integrated assays"; U.S. Apl. Ser. No. 61/149,253, filed Feb. 2, 2009, entitled "Structures for Controlling Light Interaction with Microfluidic Devices"; and U.S. patent application Ser. No. 61/138,726, filed Dec. 18, 2008, entitled "Reagent storage in microfluidic systems and related articles and methods", each of which is incorporated herein by reference in its entirety for all purposes.

Figure 1B:
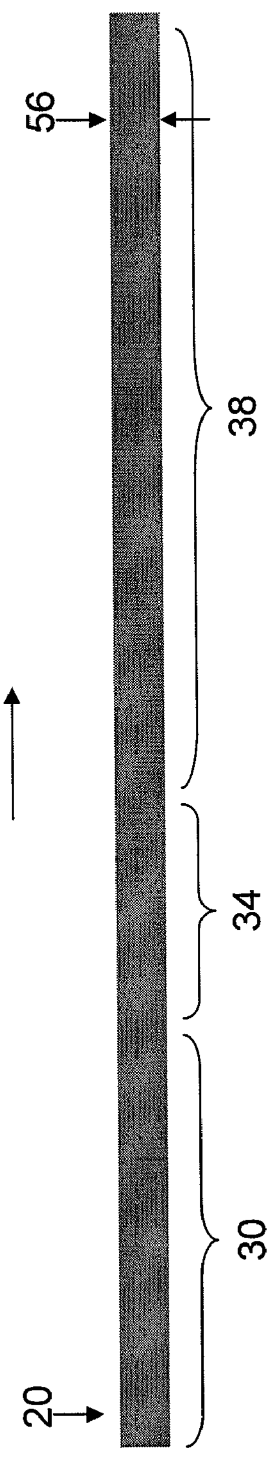

FIGS. 1A-1H show various microfluidic channels that can be used to control fluid flow in a microfluidic system according to one embodiment of the invention. FIG. 1A shows a side view and FIG. 1B shows a top view of a portion of a channel 20. As shown in the illustrative embodiment of FIG. 1A, channel 20 may include a first channel portion 30, a second channel portion 34, and a third channel portion 38. Second channel portion 34 may act as a flow constriction region as it has a smaller height, and, therefore, a smaller cross-sectional area, than those of the first and third channel portions. First and third channel portions 30 and 38 are non-constrictive to fluid flow relative to the second channel portion; that is, the first and third channel portions act as non-constriction regions in this embodiment.

In one embodiment, a low viscosity fluid 40 (e.g., a first fluid) flows in channel 20 at a first flow rate in the direction of arrow 50, as shown in FIG. 1A. The flow rate of low viscosity fluid 40 may be regulated by the smallest cross-sectional area of the channel system, such as the flow constriction region formed by second channel portion 34. As described in more detail below, in some embodiments involving substantially incompressible fluids in the channel system, the flow rate of all the fluids in the system may be equal to one another. Thus, the flow rate of portion 40A of low viscosity fluid 40 in first channel portion 30, and portion 40C in third channel portion 38, may be governed by the flow rate in second channel portion 34 (e.g., portion 40B). Likewise, high viscosity fluid 42, e.g., a second fluid having a relatively higher viscosity than that of low viscosity fluid 40, may also flow at the first flow rate as it flows in first channel portion 30. Optionally, a low viscosity fluid 44 (e.g., a third fluid), which may also have a relatively lower viscosity compared to that of high viscosity fluid 42, may follow high viscosity fluid 42 at the first flow rate.

Figure 1C:
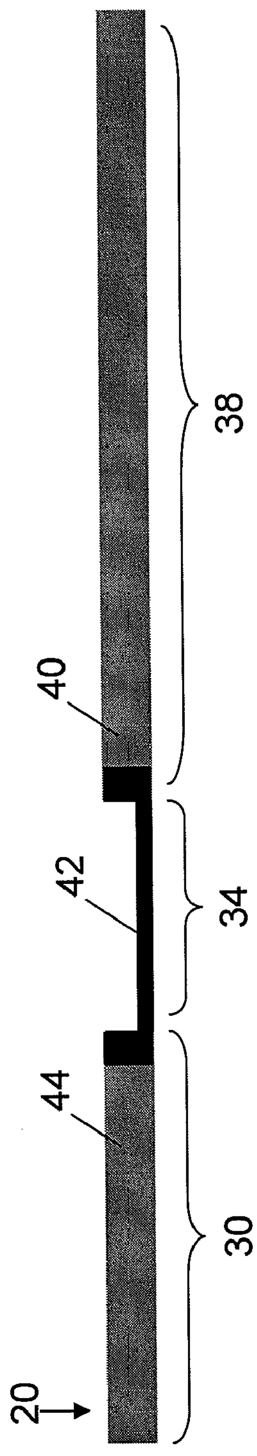
Figure 1D:
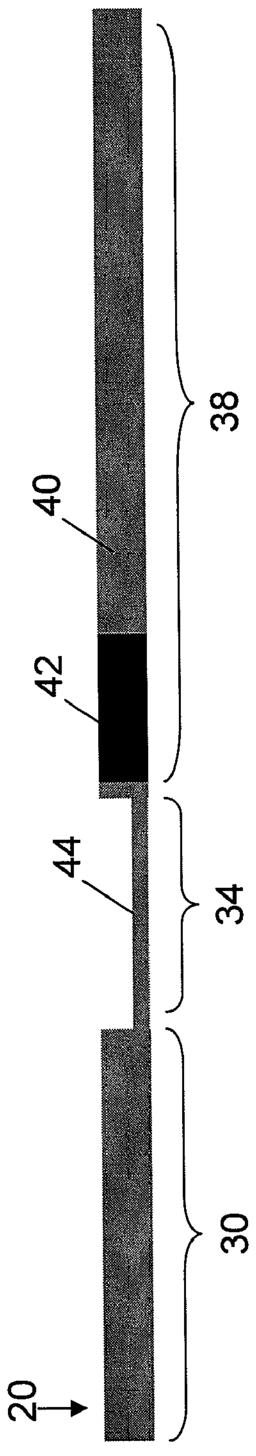

As shown in the embodiment illustrated in FIG. 1C, when high viscosity fluid 42 enters second channel portion 34, the high viscosity of the fluid causes it to flow at a second, slower flow rate than the first flow rate (which, as described above, may be governed by the flow of low viscosity fluid 40 through second channel portion 34). The introduction of high viscosity fluid 42 into second channel portion 34 causes the flow rate of the fluids in the system to decrease; i.e., low viscosity fluids 40 and 44 now flow at the second flow rate. All of the fluids may flow at the second flow rate until all or a portion of high viscosity fluid 42 flows out of second channel portion 34 and into third channel portion 38, as shown in FIG. 1D. When this occurs, low viscosity fluid 44 enters second channel portion 34, and the flow rate of the fluids in the system may now be governed by the flow rate at which fluid 44 flows through this flow constriction region.

In one embodiment, low viscosity fluid 44 has the same viscosity as fluid 40, and the act of high viscosity fluid 42 exiting the flow constriction region and low viscosity fluid 44 entering the flow constriction region cause all of the first, second, and third fluids to flow at the first flow rate. Alternatively, if low viscosity fluid 44 has a lower viscosity than that of fluids 40 and 42, the flow rate of the fluids may be higher relative to the first flow rate.

It should be understood that while in some embodiments, the flow rate of one or more fluids in a microfluidic system is governed by the flow of a fluid in a flow constriction region, in other embodiments, flow rate may be regulated by the flow of a high viscosity fluid in a non-constriction region. For instance, referring to FIG. 1A, if fluid 42 has a sufficiently high viscosity, the flow rate of the fluids may be regulated by the flow of this fluid in channel portion 30 despite the flow of fluid 40 in the flow constriction region. The control of flow rate is, therefore, determined by a balance between several factors. Without wishing to be bound by theory, the inventors believe that the following theory can be used to describe the relationship between flow rate, channel dimensions, and viscosities of fluids flowing in a channel system.

Laminar flow of an incompressible uniform viscous fluid (e.g., Newtonian fluid) in a tube driven by pressure can be described by Poiseuille's Law, which is expressed as follows:

$$Q = \frac{\pi R^4}{8\eta} \cdot \frac{\Delta P}{L} \quad \text{(Equation 1)}$$

where Q is the volumetric flow rate (in $m^3/s$, for example), R is the radius in of the tube (m), ΔP is the change in pressure across the tube (Pa), η is the dynamic fluid viscosity (Pa·s), and L is the length of the tube (m). To generalize beyond circular tubes to any closed channel, this equation can be expressed as:

$$Q = \frac{AR_H^2}{8\eta} \cdot \frac{\Delta P}{L} \quad \text{(Equation 1b)}$$

where A is the cross-sectional area of the channel and $R_H$ is the hydraulic radius, $R_H=2A/P$ with P being the parameter of the channel. For a circular tube, $AR_H^2=\pi R$. For a rectangular channel of width w and depth d, $AR_H^2=(wd)^3/(w+d)^2$.

For incompressible flow, the flow rate throughout a simple channel system must be equal. The simple channel can be conceptualized by a single microchannel with a single entrance (i.e., an inlet), a single exit (i.e., an outlet), and no connecting channels (i.e., no channel intersections). The flow rate at the inlet of the channel must equal the flow rate at the outlet, as there is no storage or compression of the fluid. That flow rate will be set by Poiseuille's Law or a variant thereof to match the shape factor of the channel.

As can be seen in Equations 1 and 1b, flow rate is directly proportional to the shape factor of the channel, which is a very strong function of the effective radius. A channel of very small effective radius slows down flow significantly. In a microchannel with different cross-sectional areas, given a constant pressure, the flow rate of a single fluid in the channel will be controlled by the smallest cross-sectional area (i.e., a flow constriction region) of the channel system.

As can also be seen from Equations 1 and 1b, the flow rate of a fluid through a tube or channel is an inverse function of that fluid's viscosity. Through a given length of channel with the same pressure drop across the inlet and outlet, a plug of a high viscosity fluid will move more slowly than a similarly sized plug of a relatively lower viscosity fluid. In fact, the difference in flow rate can be calculated as:

$$\frac{Q_A}{Q_B} = \frac{\eta_B}{\eta_A} \text{ or } Q_A = \frac{\eta_B}{\eta_A} \cdot Q_B \quad \text{(Equation 2)}$$

A first fluid having a viscosity 100 times higher than the viscosity of a second fluid will flow at a flow rate of 1/100 times the flow rate of that of the second fluid through the same channel. This feature can have many uses in multi-component flows (e.g., flows of plugs of multiple fluids), particularly if at least two fluids in the system have significantly different viscosities (such as the factor of 100 shown above).

If the components of flow are substantially incompressible (a reasonable assumption in some microfluidic systems), the flow rate of all the fluids in the system will be equal to one another. In the simple microchannel system described above with a single inlet, a single outlet, no connecting channels, and with a single flow constriction region with the remaining sections of the channel having a relatively larger shape factor, the flow rate of the entire system may be controlled by the flow rate through the flow constriction region. For example, when a fluid of low viscosity (e.g., fluid 40 of FIG. 1A) is flowing through the flow constriction region (e.g., second channel portion 34), it will flow relatively quickly, and the volumetric flow rate of each fluid in the system will be relatively high. When a fluid of high viscosity (e.g., fluid 42) flows through the same flow constriction region, its flow rate will be much lower (e.g., by a factor equal to the ratio of viscosities of the first and second fluids), and thus the flow rate of each fluid in the system will be low.

To determine the flow rate of multiple fluids in a channel having varying cross-sectional areas, the flow rate can be determined by comparing the ratio of channel dimensions to viscosity of the fluids. For instance, referring to FIG. 1A, the flow rate $Q_1$, of low viscosity fluid 40 in the flow constriction region (channel portion 34) is proportional to the channel dimensions of channel portion 34 over the viscosity of fluid 40 (e.g., $Q_1 \sim A_1 R_1{}^2{}_H/\eta_1$) according to Equation 1b. The flow rate of, $Q_2$, high viscosity fluid 42 in channel portion 30 is proportional to the channel dimensions of channel portion 30 over the viscosity of fluid 42 (e.g., $Q_2 \sim A_2 R_2{}^2{}_H/\eta_2$). The flow rate of the two fluids may be governed by the slowest calculated flow rate $Q_1$ or $Q_2$. Thus, if $Q_1<Q_2$, the influence of the constriction region is greater than the influence of the high viscosity of fluid 42 on fluid flow. As a result, the flow rate of both fluids 40 and 42 may be regulated by the flow of fluid 40 in the flow constriction region, rather than by high viscosity fluid 42 flowing in the non-constriction region.

Accordingly, appropriate channel dimensions and viscosities of fluids can be chosen to regulate fluid flow in a channel system in a particular manner. For example, in some embodiments, these parameters can be chosen such that the flow rate in a microfluidic system is always regulated by the flow of fluids in a flow constriction region whether the fluids are high- or low viscosity fluids. That is, the flow rate of one or more fluids will be regulated according to which fluid is flowing in the flow constriction region. In other embodiments, flow rate is regulated in a microfluidic system by the flow of a high viscosity fluid, whether it be in a flow constriction region or a non-constriction region.

Figures 1E, 1F, 1G, 1H:
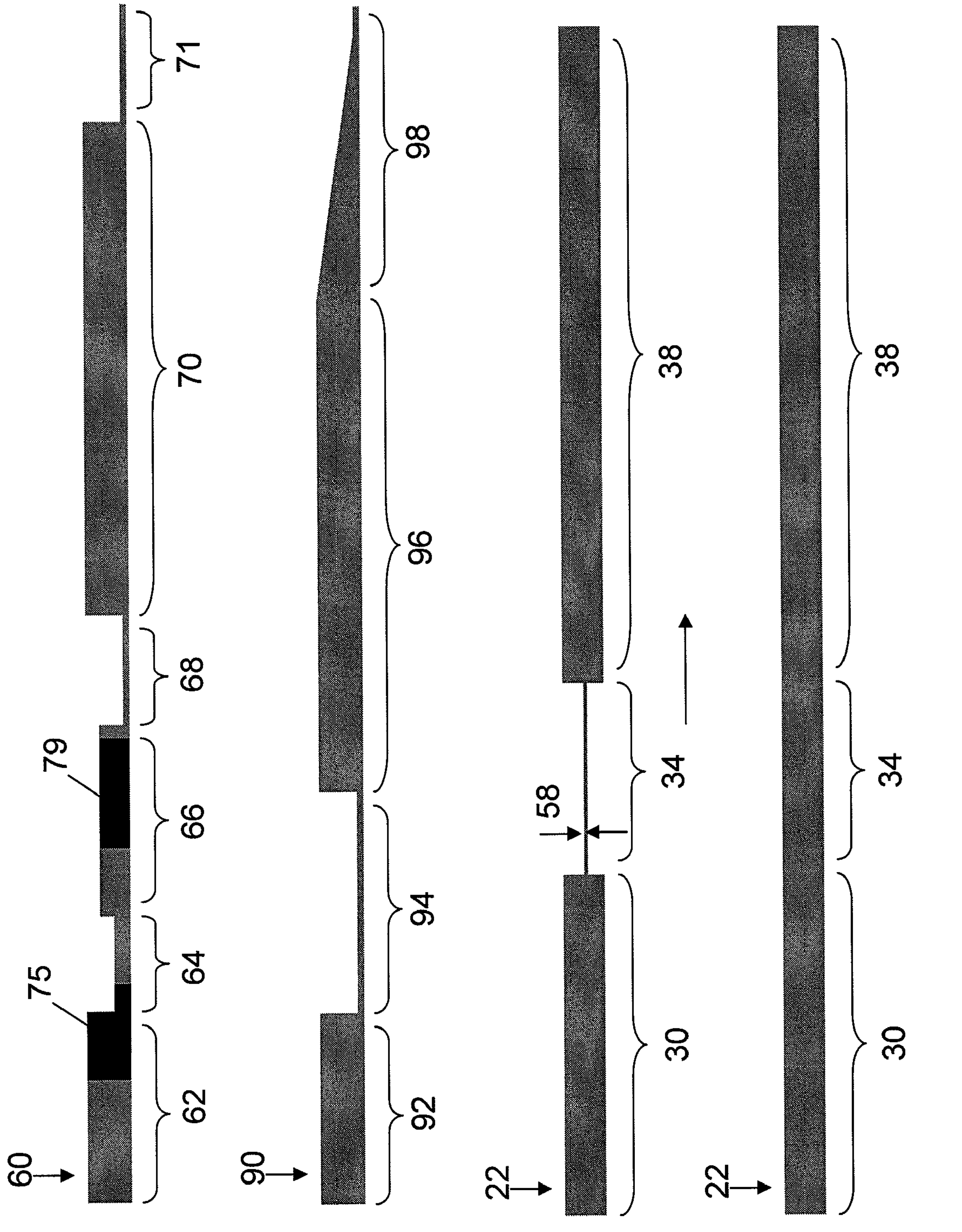

As shown in the embodiment illustrated in FIG. 1E, a channel may have several channel portions of varying cross-sectional dimensions, such as channel portions 62, 64, 66, 68, 70, and 71, which can be used to control the rate of fluid flow. As illustrated, a channel may include more than one non-constriction regions (e.g., channel portions 62 and 70), as well as several channel portions that may act as flow constriction regions (e.g., channel portions 64, 66, 68, and 71). In such a system, the flow rate of the fluids may be controlled by the smallest ratio of channel dimensions to viscosity of the fluids, as described above.

In some embodiments, particular fluid viscosities and channel dimensions of a microfluidic system can be chosen such that the flow rate of the fluids is controlled by which channel portion the highest viscosity fluid resides, and is independent of which channel portion a low viscosity fluid resides. For instance, a high viscosity fluid flowing in channel portion 68 of FIG. 1E may cause the fluids to flow at the slowest flow rate, while the high viscosity fluid flowing in the non-constriction regions may result in the fluids to flow at the highest flow rates. Flow of the high viscosity fluid in channel portions 64, 66, and 71 may cause the fluids to flow at intermediate flow rates.

In other embodiments, the limiting factor in regulating the flow rate of the fluids may depend, in part, on which channel portion the low viscosity fluid resides. For example, a low viscosity fluid flowing in a first flow constriction region can cause the fluids to flow at a slower flow rate than a high viscosity fluid flowing in a second flow constriction region (e.g., the first flow constriction region may have a smaller cross-sectional area than the second flow constriction region).

In more complicated systems, the overall flow velocity of the fluids can be determined by the flow of more than one plugs of high viscosity fluid. For example, in the embodiment shown in FIG. 1E, high viscosity fluids 75 and 79 have the same viscosity and are separated by a low viscosity fluid. High viscosity fluid 75 may control the flow rate of the fluids as it enters channel portion 64, as this channel portion is more constrictive to fluid flow compared to channel portion 66, where high viscosity fluid 79 resides. However, as high viscosity fluid 79 enters into channel portion 68, the flow velocity of the fluids will be controlled by this high viscosity fluid, as channel portion 68 is more restrictive to fluid flow than channel portion 64.

As described in more detail below, the rate of change of fluid flow (e.g., the deceleration and acceleration of fluid flow) may also be controlled (e.g., increased or decreased) by choosing appropriate viscosities and channel dimensions. Deceleration of fluid flow may be caused by the introduction of a relatively high viscosity fluid into a flow constriction region. Acceleration of fluid flow may be caused by the exiting of the relatively high viscosity fluid from a flow constriction region into a region that is less constrictive to fluid flow. For example, in reference to FIG. 1F, a high viscosity fluid flowing from channel portion 92 to channel portion 94 can result in a high rate of deceleration of fluid flow since the change in cross-sectional dimensions between channel portions 92 and 94 is abrupt. On the other hand, fluid flow may have a lower rate of deceleration when the high viscosity fluid flows from channel portion 96 to channel portion 98, as the changes in cross-sectional dimensions between these channel portions is gradual. Applications involving high rates of deceleration of fluid flow are described below.

Accordingly, in systems described herein, the cross-sectional dimensions and configurations of the channel portions, the spacing of the channel portions, the length of the channel portions, the volume of the high and low viscosity fluids, and the spacing between two or more fluids can be chosen to determine the flow rate of a fluid, the time at which the fluid reaches a particular region of the microfluidic system, the rate of change of fluid flow, and/or the amount of time the fluid resides in that particular region. Such systems can offer control of flow velocity without the use of moving parts (e.g., valves) and/or without external control (e.g., changing flow rate by using pumps or vacuums that vary pressure).

Although FIGS. 1A-1F show flow constriction regions in the form of channel portions having a smaller height than non-constriction regions, it should be understood that any suitable constriction to fluid flow can be used in microfluidic systems described herein. For instance, while channel 20 may have a substantially uniform width 56 as shown in the top view of channel 20 in FIG. 1B, in other embodiments, a channel including a flow constriction region may have a non-uniform width, as illustrated in the top view shown in FIG. 1G. Channel 22 of FIG. 1G includes a second channel portion 34 comprising a narrow channel having a width 58 that serves as a flow constriction region. The height of each of the channel portions of channel 22 may be substantially the same, as illustrated in the side view of channel 22 shown in FIG. 1H, or in other embodiments, the height of second channel portion 34 may be smaller than the other channel portions, as shown in FIGS. 1A, 1C, and 1D. In yet other embodiments, the height of channel portion 34 may be larger than the height of channel portions 30 and 38. In the systems described above and herein, second channel portion 34 acts as a flow constriction region as long as it is more restrictive to fluid flow compared to a non-constriction region. In some cases, greater restriction to fluid flow is caused by the cross-sectional area of the fluid path defined by channel portion 34 being smaller than the cross-sectional area of the fluid path defined by channel portions 30 and/or 38.

As described herein, the amplitude of the change in cross-section between a flow constriction region and a non-constriction region may have a significant impact on the change in flow rate. The combination of a reduction in channel width and channel height will have a greater impact than a reduction in width or height alone. This effect is described by the following equation:

$$Q=(\Delta P/8\eta)(AR_h^2/L) \quad \text{(Equation 3)}$$

$$\text{with } R_h=2A/p, \quad \text{(Equation 4)}$$

where Q is the volumetric flow rate, ΔP the pressure drop, η the viscosity, A the cross-sectional area of the channel, p the perimeter of the channel, and L the length of the channel. Thus, in some embodiments, it is advantageous to design flow constriction regions having both a reduction in width and a reduction in height in order to reduce the cross-sectional area of the fluid path and achieve large changes in volumetric flow rates.

It should be understood that a flow constriction region may include any suitable configuration that causes a change (e.g., decrease) in velocity of a fluid flowing through the region compared to when the fluid is not flowing through the flow constriction region. For example, a flow constriction region may have a height and/or a width of less than 500 microns, less than 200 microns, less than 100 microns, less than 75 microns, less than 50 microns, less than 30 microns, less than 25 microns, less than 15 microns, less than 10 microns, or less than 5 microns. Some such dimensions can allow the flow constriction region to have a cross-sectional area that is at least 3, 5, 10, 15, 25, 50, 75, or 100 times smaller than a cross-sectional area of an adjacent non-flow constriction region. The cross-sectional dimensions of a flow constriction region may be chosen, for example, to achieve a certain reduction in flow rate or a certain average rate of deceleration or acceleration of fluids, as described in more detail below.

In addition, a flow constriction region may have any suitable length in a microfluidic system. Typically, a longer length of a flow constriction region will cause the fluids to flow at a lower flow rate (e.g., assuming a viscous fluid flows in the flow constriction region) for a longer period of time. This can allow, for example, a component to interact at an analysis region for a prolonged period of time as described in more detail below. The amount of time a fluid spends in a region of the system can be predetermined or pre-calculated in part by knowing the dimensions of the channel, the viscosities of the fluids being flowed, and the pressure differential between the inlet and the outlet. Accordingly, a flow constriction region may have a length of at least 1 mm, at least 5 mm, at least 1 cm, at least 2 cm, at least 5 cm, at least 10 cm, at least 20 cm, or at least 50 cm, and may be linear, serpentine, or may have any other suitable shape as necessary or desired.

Although flow constriction regions comprising channel portions having a smaller height and/or width are presented in FIGS. 1A-1H, in other embodiments, a flow constriction region can include a channel portion that has the same width and/or height as a non-constriction region. In some such embodiments, the channel portion of the flow constriction region may include one or more flow constriction elements positioned therein. The flow constriction element(s) can effectively cause the cross-sectional dimension of the fluid flow path of the channel portion to be smaller than that of a non-constriction region.

Figure 2A:
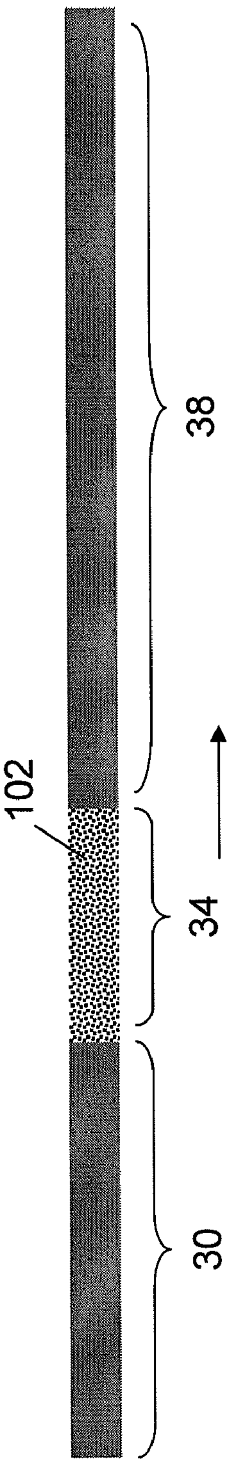
FIGS. 2A-2C show various microfluidic channels including flow constriction regions having flow constriction elements that can be used to control fluid flow in a microfluidic system according to one embodiment of the invention.

As shown in the embodiment illustrated in FIG. 2A, channel portion 34 acts as a flow constriction region by containing a plurality of beads or particles 102 that cause the flow path within the region to be substantially smaller than channel portions 30 and 38 (e.g., non-constriction regions). Because beads or particles 102 occupy space within channel portion 34, there is less volume for fluid flow within this channel portion compared to the non-constriction regions. Thus, the cross-sectional area of the fluid path within channel portion 34 (e.g., the combined fluid paths of the interstices/porous regions between the beads or particles) is less than the cross-sectional area of the fluid path defined by channel portions 30 or 38. The cross-sectional area of the fluid path of channel portion 34 and/or the resistance to fluid flow can be changed, for example, by varying the size or packing of the beads or particles, and/or by varying the affinity of the beads or particles to the fluids being flowed in the channel.

Figure 2B:
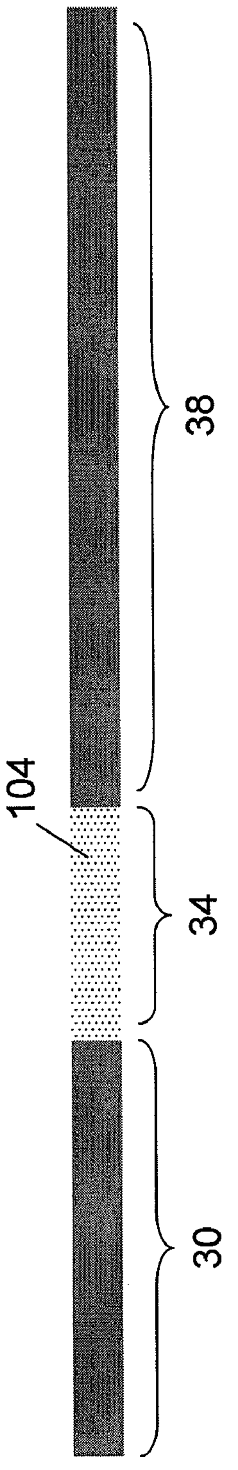

As shown in the illustrative embodiment of FIG. 2B, a flow constriction region may include a gel 104 in some embodiments. The gel matrix also causes the cross-sectional area of the fluid flow paths defined by the interstices of the gel to be smaller than the cross-sectional area of the fluid flow paths defined by channel portions 30 and 38. The cross linking density and the chemical composition of the gel matrix are examples of parameters that can be changed in order to vary the resistance to fluid flow, and, therefore, the flow rate of a fluid flowing in the flow constriction region.

Figure 2C:
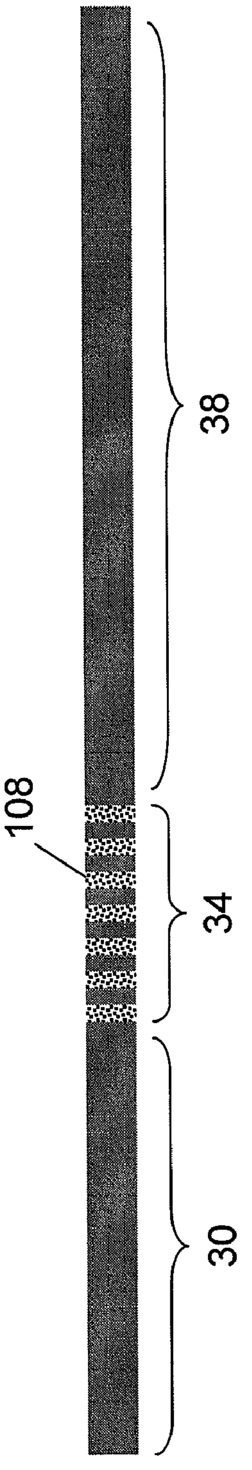

As illustrated in FIG. 2C, channel portion 34 may include a plurality of pillars 108 that affectively reduce the cross-sectional area of the fluid flow path within this channel portion. The pillars may extend from a top surface to a bottom surface of the channel, or may extend partially from a single surface of the channel in any suitable configuration (e.g., patterned or non-patterned). It should be understood that the flow constriction regions illustrated in FIGS. 2A-2C are exemplarily and that other fluid constriction elements can be incorporated into microfluidic systems described herein. In addition, flow constriction regions can be positioned in any suitable position in a microfluidic system. For example, a flow constriction region may be positioned upstream or downstream of other components of the microfluidic system such as an analysis region, liquid containment region, inlet, outlet, etc.

The methods illustrated in connection with FIGS. 3A-3F and with other embodiments described herein may be useful for certain solution-phase reactions that may be difficult to perform in some microfluidic systems. Many immunoassay formats are especially difficult to perform in microchannels due to the need to stop flow or substantially reduce flow rate. For example, in a standard enzyme-linked immunosorbent acid (ELISA) assay, an enzyme linked to an antibody attached to a captured biomarker drives a reaction in the solution surrounding the captured structure, creating a reaction product that is potentially optically visible. In a static reaction environment, such as a microwell, the quantity of reaction product builds up in the reaction area to a level detectible by various optical devices. In certain microfluidic systems, flow must be stopped or slowed down sufficiently to allow a detectible signal to be developed, otherwise reaction product is washed away downstream. The result is that insufficient reaction product remains in the analysis region. In addition, in systems including multiple detection areas, reaction product could get washed into other areas, contaminating those areas and making independent measurements impossible. Stopping or substantially reducing flow rate in such a system can be difficult.

In addition, in some microfluidic systems, a relatively large volume of a sample or test fluid may be required to allow sufficient time for interaction of components. This is because analyses in microfluidic systems usually take place while the test fluid is flowing and/or because the nature of the interaction requires a certain amount of time in order to reach steady state (or, in order to obtain a signal that can be analyzed). For example, in some assays, a few minutes may be required to allow sufficient binding between components, especially for interactions involving a component in a fluid and a component disposed on a surface of an analysis region. The faster the flow rate of the test fluid, the more test fluid is required in order to allow the test fluid to pass over the analysis region for a specific amount of time; however, a slower flow rate means a longer waiting period before the analysis is completed.

Using methods and devices described herein, an analysis may be completed in a relatively short amount of time using only a small amount of test fluid since the test fluid can flow slowly in an analysis region, but quickly when flowing in other regions of the device. The amount of time it takes the fluids to flow through certain regions of the device may be controlled by choosing appropriate viscosity of fluids, cross-sectional area(s) of constriction region(s), and volume of fluids. In addition, the methods and devices described herein can mimic a static reaction environment similar to that of microwell-based assays, with pre-washing, post-washing, and other preparation steps familiar to conventional microfluidic systems. The shift between these two different environments can take place, in some embodiments, without the use of moving parts (e.g., valves) and/or without external control (e.g., the use of pumps or vacuums that vary pressure/flow rate in the system).

Figures 3A, 3B, 3C, 3D:
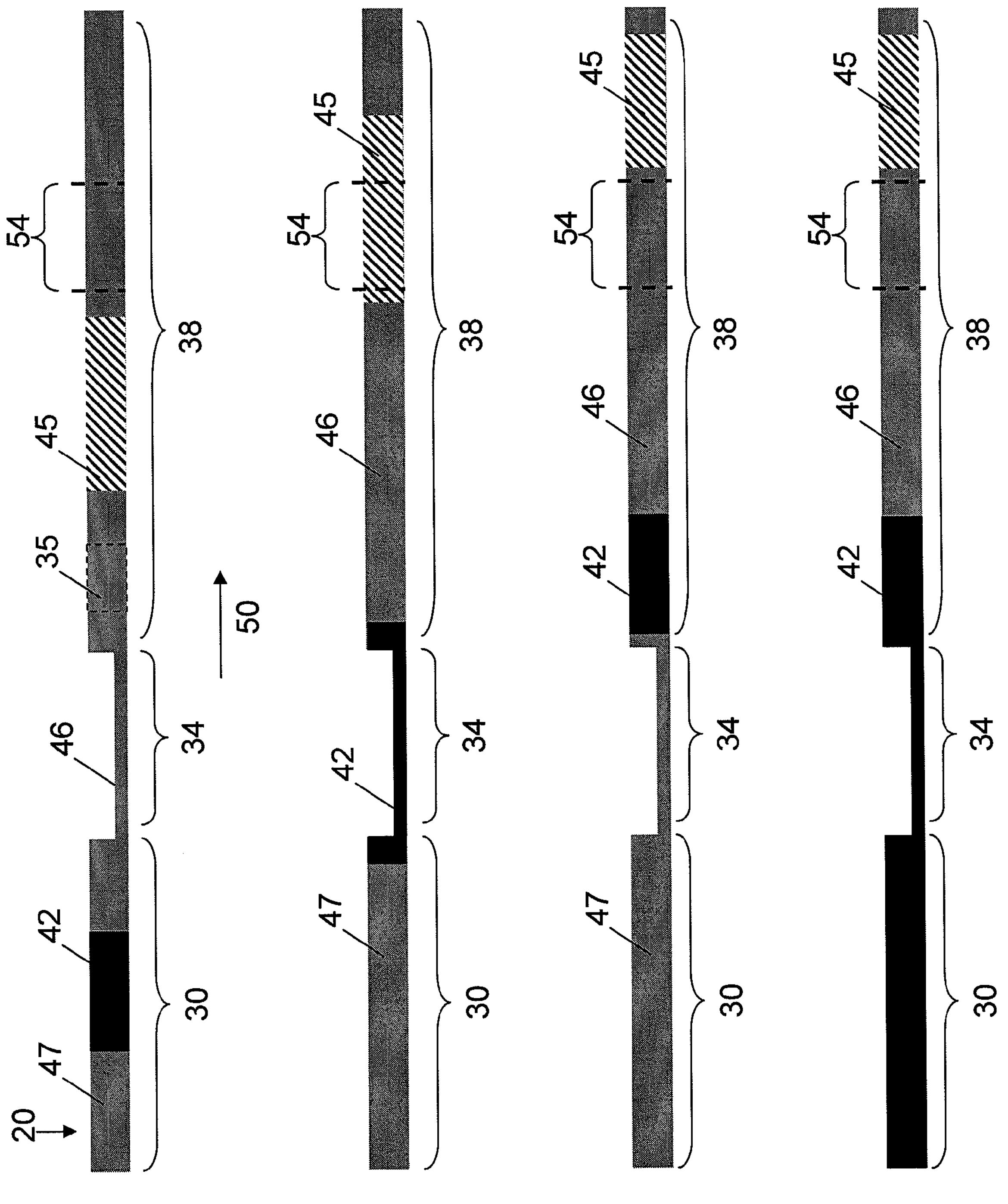
FIGS. 3A-3F show velocity control of fluids in microfluidic systems according to one embodiment of the invention.

As mentioned, velocity control can be useful when performing chemical and/or biological assays as well as other applications that require specific fluids to flow over a particular area (e.g., an analysis region) for a set amount of time. As shown in the embodiments illustrated in FIGS. 3A-3D, a method of controlling fluid flow in a channel may involve flowing a first fluid 42 (e.g., a high viscosity fluid) in a channel portion 30 of microfluidic channel 20. Meanwhile, a second fluid 45 (e.g., a "test fluid", a fluid including components to be reacted or analyzed) may be flowed in channel portion 38. Second fluid 45 may be introduced into channel portion 38 via channel portions 30 and 34, or, in other embodiments, via an intersecting channel 35, of which a cross section is shown in FIG. 3A. The flow rate of the fluids in the embodiment illustrated in FIG. 3A may be controlled by a third fluid 46 (e.g., a fluid having a lower viscosity than that of the first and/or second fluids), flowing in channel portion 34, which acts a flow constriction region. The fluids flow at a first flow rate in the direction of arrow 50 until first fluid 42 enters into the flow constriction region of channel portion 34. As this takes place, each of fluids 42, 45 and 46 flow at a second, slower flow rate.

As shown in the embodiment illustrated in FIG. 3B, first fluid 42 (e.g., a high viscosity fluid) remains in the flow constriction region for a relatively long period of time due to the slow flow velocity of the high viscosity fluid through this region. At this point in time, second fluid 45 has reached analysis area 54 (i.e., a region in which a chemical and/or biological reaction and/or analysis of a fluid component can take place) and remains at the analysis region as long as first fluid 42 remains in the constriction region. Advantageously, this can allow one or more components of second fluid 45 to interact at the analysis region for a sufficient amount of time to effect a chemical and/or biological reaction to a desired extent. For example, in one exemplary embodiment, second fluid 45 includes one or more components that can be involved in a chemical and/or biological reaction with a component of analysis region 54. A component of second fluid 45 may be a binding partner, which can bind or interact with a complementary binding partner disposed within (e.g., on a surface of) analysis region 54. Thus, when second fluid 45 flows through analysis region 54, the interaction between the binding partners can take place. In some embodiments, the flow rate of the fluids may be so slow (e.g., on the order of a few nanoliters per second) while the high viscosity fluid flows through the flow constriction region, that the system mimics a static environment.

As illustrated in FIG. 3C, after second fluid 45 has passed through analysis region 54 for an appropriate amount of time, the system may be designed such that first fluid 42 exits the flow constriction region into channel portion 38. This can stop additional component interactions from occurring at the analysis region. Meanwhile, the flow constriction region may be filled with fluid 47, which can cause the fluids to flow at a relatively higher flow rate in the microfluidic system. Fluid 47 may be, for example, a low-viscosity, high velocity fluid such as a buffer, which may be useful for washing off non-specific binding at the analysis region. A high velocity fluid such as a buffer may also be used to pre-wash a surface (e.g., an active surface within a microchannel) before performing the analysis.

In other embodiments, a surface of an analysis region is not washed after effecting a chemical and/or biological reaction, since doing so would wash away any signal that has been built up within the region. In some such cases, the test fluid remains at the analysis region while a measurement of the chemical and/or biological reaction is obtained. In other cases, the test fluids exits the analysis region and the analysis region is filled with a different fluid (e.g., a high- or low viscosity fluid), which can reduce the amount of background noise within the analysis region 54 while a measurement is being performed. The system may be designed such that the fluid flows slowly enough through the analysis region to prevent washing away of the signal in the region. For instance, as shown in the exemplary embodiment of FIG. 3D, third fluid 46 may replace second fluid 45 (e.g., a test fluid) in the analysis region, but may flow slowly through the analysis region as first fluid 42 remains in the flow constriction region.

As illustrated in FIGS. 3A-3D, a test fluid (e.g., second fluid 45) and a high viscosity fluid (e.g., first fluid 42) may be separated by a separation fluid (e.g., third fluid 46). A separation fluid may be useful to separate fluids and to prevent contamination between fluids during an analysis. In addition, if a device includes stored reagents, by maintaining a separation fluid between each of the reagents in a reagent storage area, the stored fluids can be delivered in sequence from the reagent storage area while avoiding contact between any of the stored fluids. Any separation fluid that separates the stored reagents may be applied to the analysis region without altering the conditions of the analysis region. For example, if antibody-antigen binding has occurred at an analysis region, air can flow through this region with minimal or no effect on any binding that has occurred.

In some embodiments, all of the fluids used in a device are incompressible; however, in other embodiments, one or more of the fluids is compressible. For instance, a separation fluid may be in the form of a compressible gas (e.g., air, nitrogen, oxygen, etc.). In addition, in some cases all of the fluids used in a device are miscible, but in other cases, one or more of the fluids is immiscible or only slightly miscible. For instance, a separation fluid may be in the form of an organic solvent or a fluorinated solvent (e.g., poly(dimethylsiloxane) and poly(trifluoropropylmethysiloxane)).

Figure 3E:
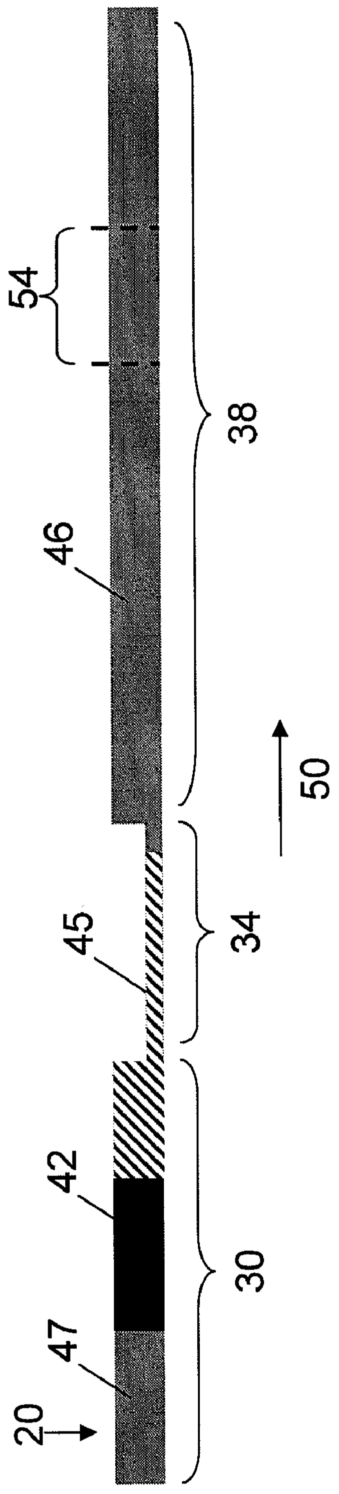
Figure 3F:
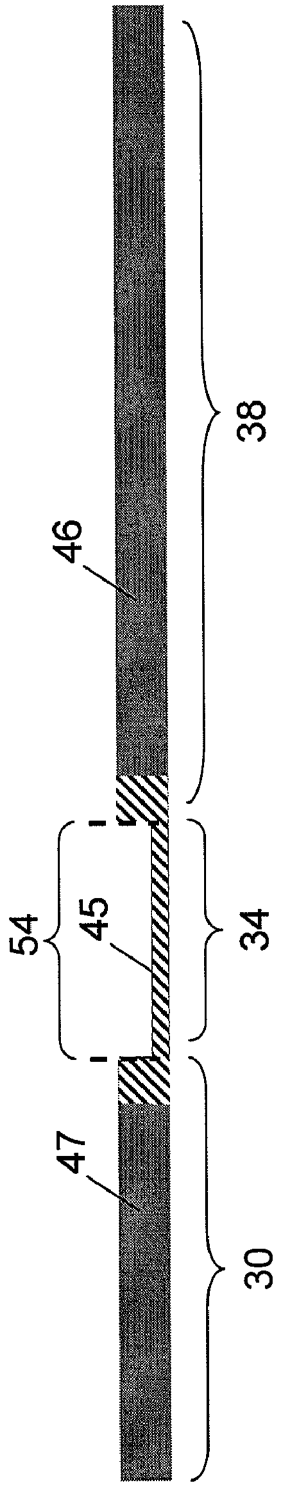

In another embodiment, a test fluid and a high viscosity fluid are positioned immediately adjacent one another in a microfluidic system, as shown in the embodiment illustrated in FIG. 3E. In this configuration, there is no need for separation fluid, making the technique applicable to simpler assay procedures that do not require such fluid(s) to prevent contamination.

Sometimes, a test fluid is a relatively high viscosity fluid and is used to control the rate of fluid flow in a microfluidic system. For example, as shown in the exemplary embodiment of FIG. 3F, fluid 45 (e.g., a test fluid such as blood, serum, plasma, tear fluid, saliva, urine, sperm, sputum, or any other fluid of interest that may include a component to be reacted and/or analyzed) may be more viscous than another fluid 46 (e.g., a low viscosity fluid such as a buffer) in the microfluidic system. Thus, when fluid 46 flows through the constriction region defined by channel portion 34, the fluids flow at a relatively higher flow rate; when fluid 45 flows through the same channel portion, the fluids flow at a relatively lower flow rate. In some embodiments, a flow constriction region can include an analysis region 54 so that while the test fluid is flowing slowly through the flow constriction region, a chemical and/or biological interaction takes place at that region. This and other configurations can allow the interaction to occur for a longer period of time at the analysis region compared to the same fluids flowing in a microfluidic system without the flow constriction region. For example, the use of a flow constriction region and/or a viscous fluid can allow an interaction of a component to occur at least 3 times, at least 5 times, at least 10 times, at least 20 times, at least 35 times, at least 50 times, at least 70 times, or at least 100 times longer at a region (e.g., an analysis region) as a result of a fluid (e.g., a relatively high viscosity fluid) flowing from one channel portion to another, compared to the absence of that fluid flowing from the one channel portion to the other. This can allow an interaction to occur at an analysis region for at least 5 seconds, at least 15 seconds, at least 30 seconds, at least 60 seconds, at least 2 minutes, at least 5 minutes, at least 15 minutes, or at least 30 minutes, for example. Cell-based assays and other interactions may be performed in this manner.

A multitude of variations can be made to the devices and methods described above. For example, in one embodiment, the sample is blood and a plug of higher viscosity fluid such as glycerol can be used to slow flow. In contrast, with the same sample, a plug of lower viscosity fluid such as air (a compressible fluid) can be used to accelerate flow. Multiple plugs of different viscosity fluids could be used to provide different flow rates (and thus velocities).

As described herein, a flow rate of a fluid may decrease (or increase) substantially due to factors such as the difference between the viscosities of fluids, the cross-sectional areas of channel portions (and/or fluid flow paths within the channel portions). For instance, a volumetric flow rate of a fluid (e.g., a sample of interest and/or a high viscosity fluid) may decrease (or increase) by a factor of at least 3, at least 5, at least 10, at least 15, at least 25, at least 35, at least 40, at least 50, at least 75, at least 85, or at least 90 in the microfluidic system as a result of a fluid flowing from a first channel portion to a second channel portion, compared to the absence of flowing the fluid from the first channel portion to the second channel portion. In some embodiments, the above-mentioned decreases or increases in flow rate can take place in less than 30 seconds, less than 20 seconds, less than 10 seconds, less than 5 seconds, less than 3 seconds, less than 2 seconds, or less than 1 second. Flowing a fluid having a relatively higher viscosity from a non-constriction region to a flow constriction region can cause the flow rate to decrease, while flowing the fluid from a flow constriction region to a non-constriction region can cause the flow rate to increase (e.g., assuming a relatively lower viscosity fluid enters the flow constriction region in place of the higher viscosity fluid). Similarly, a relatively low viscosity fluid can be used to increase the velocity of high viscosity fluids by allowing the low viscosity fluid to enter a flow constriction region from a non-constriction region (e.g., assuming the low viscosity fluid enters the flow constriction region in place of the higher viscosity fluid). In some embodiments, such and other examples of increasing and decreasing flow rate can be performed without completely stopping the one or more fluids.

It should be understood that any suitable fluid can be used as first, second, third, fourth, etc. fluids and such fluids may include one or more samples to be tested, components to be interacted, buffers, reagents, and the like. In addition, such fluids may serve simultaneously as a sample and a high viscosity fluid, as a sample and a low viscosity fluid, as a buffer and a low viscosity fluid, as a separation fluid and a high viscosity fluid, as separation fluid and a high viscosity fluid, as a separation fluid and a compressible or incompressible fluid, etc.

A variety of fluid viscosities can be used to control flow rates of fluids in microfluidic systems described herein. For example, a fluid may have a viscosity of at least 5 mPa·s, at least 15 mPa·s, at least 25 mPa·s, at least 30 mPa·s, at least 40 mPa·s, at least 50 mPa·s, at least 75 mPa·s, at least 90 mPa·s, at least 100 mPa·s, at least 500 mPa·s, at least 1000 mPa·s, at least 5000 mPa·s, or at least 10,000 mPa·s. Very high viscosity fluids may be used when it is desirable to mimic stoppage of fluid flow in the microfluidic system. Non-limiting examples of fluids that can be used as relatively high viscosity fluids include glycerol/water mixtures, liquid polymers (such as liquid PDMS or other silicone oils), aqueous solutions of polymers such as poly(vinyl alcohol) or poly(acrylic acid), aqueous solutions of biopolymers such sucrose or dextrin, and solutions of polymer in organic solvents such as polystyrene in dimethylsulfoxide. The formulation of these high-viscosity fluids can be adjusted to reach pre-determined viscosities. For example, the viscosity of glycerol/water mixtures can be adjusted between, e.g., about 0.89 mPa·s and about 934 mPa·s (at 25° C.). Liquid PDMS can be selected with viscosities ranging from, e.g., about 6 mPa·s (Fluka AS4) to about 1000 mPa·s (Fluka AR1000). Non-limiting examples of fluids that can be used as relatively low viscosity fluids include water, air, buffer solutions, and perfluorodecadin. Body fluids such as blood, serum, sputum, urine, sperm, feces can serve as relatively low viscosity fluids or high viscosity fluids, e.g., depending on the other fluids present in the system.

In embodiments involving more than one fluid in the microfluidic system, a first fluid and a second fluid may have different viscosities. In some cases, the viscosities of the first and second fluids differs by a factor of at least 3, at least 5, at least 10, at least 15, at least 25, at least 40, at least 50, at least 75, at least 85, at least 90, at least 100, at least 120, at least 130, at least 150, at least 300, at least 500, or at least 1000. As described herein, the types of fluids and viscosities of fluids can be predetermined and pre-calculated prior to use based on, for example, the flow rates to be achieved, the average rate of deceleration/acceleration, the type of assay, and the geometry of the microfluidic system. Such calculations can be performed by those of ordinary skill in the art using general knowledge known in the art in combination with the description contained herein.

In addition, a fluid may have any suitable volume and/or length in a microfluidic channel. For instance, a fluid may have a volume of at least 10 pL, or in other embodiments, at least 0.1 nL, at least 1 nL, at least 10 nL, at least 0.1 µL, at least 1 µL, at least 10 µL, or at least 100 µL.

In some embodiments, the methods described in connection with FIGS. 3A-3F and with other systems described herein are performed while applying a substantially constant non-zero pressure drop (i.e., ΔP) across an inlet and an outlet of a microfluidic system. A substantially constant non-zero pressure drop can be achieved, for example, by applying a positive pressure at the inlet or a reduced pressure (e.g., a vacuum) at the outlet. In some cases, a substantially constant non-zero pressure drop is achieved while flow does not take place predominately by capillary forces and/or without the use of actuating valves (e.g., without changing a cross-sectional area of a channel of fluid path of the microfluidic system).

Systems including application of a substantially constant non-zero pressure drop can be contrasted with capillary flow systems, which typically involve a changing pressure drop across a channel system, as well as electrophoresis-based systems, which do not require application of a pressure drop. It should be understood, however, that in certain embodiments, methods described herein can be performed with a changing pressure drop across an inlet and an outlet of the microfluidic system by using capillary flow, the use of valves, or other external controls that vary pressure and/or flow rate.

In some cases, a substantially constant pressure drop is established in a microfluidic system including only a single inlet and a single outlet. In addition, systems may be designed such that one or more fluid constriction regions do not build up pressure upon operation, such as by clogging of a flow constriction region with components of a fluid or by actuating a valve so that pressure builds up in the system. To achieve such a system, a high viscosity fluid may be chosen such that its viscosity is not too high so as to clog a flow constriction region.

Microfluidic systems described herein may optionally include a bypass channel, i.e., a channel that is connected to an upstream portion and a downstream portion of a channel segment that allows a fluid to bypass the channel segment. Thus, if the channel segment becomes clogged, a fluid can flow in the bypass channel to reach the downstream portion of the channel segment. In some embodiments, methods and devices described herein do not involve the use of bypass channels.

As described herein, flow constriction regions and fluids (e.g., in the form of plugs) of differing viscosities can be used to time flow in microfluidic systems. For instance, in some embodiments, given a constant pressure drop across a microfluidic system, a plug of high viscosity fluid can be appropriately sized along with a flow constriction to slow flow for a defined amount of time. A series of flow constrictions or plugs of fluid can be used to program complex timing of reagents in a flow system. Viscosity, plug length (e.g., volume), constriction length and diameter, for example, can be set to determine timing, and programming can be accomplished by adjusting these parameters, as well as by designing the microfluidic system to have a particular configuration. Polymerase chain reaction (PCR) is one example of an assay format that requires complex timing and which may benefit from a "flow-clock" in a microfluidic system; however, the methods and devices described herein are applicable to any assay or interaction where timing of reagents is important. Timing may be an important variable in, for example, assays, including immunoassays, cell capture and counting, general chemistry tests, etc.

For example, referring to FIGS. 3A-3E, the length of time that fluid 45 (e.g., a test fluid) remains in reaction area 54 can be controlled predominately by the length of time that fluid 42 (e.g., a high viscosity fluid) remains in the flow constriction region. Thus, if the goal is to allow interaction of two components at the analysis region for a defined period of time (e.g., to allow a timed reaction to occur), the volume and viscosity of fluid 42, as well as the dimensions (e.g., cross-sectional area and length) of the flow constriction region, can be predetermined to achieve this goal. Of course, the volume of fluid 45, the dimensions of the analysis region, and the pressure drop between the inlet and the outlet can also be predetermined in a similar fashion. Additionally, the timing of other reagents such as buffers, wash solutions, amplification reagents, markers, etc. can be controlled in this manner. This is one example of how methods and devices described herein can be used for viscosity-programmed velocity control and for achieving timing of reagents, e.g., even while a constant non-zero pressure drop is applied across an inlet and an outlet of a microfluidic system. The timing of reagents can also be achieved for the configuration shown in FIG. 3F.

Devices that are designed with particular geometries and for use with particular volumes and viscosities of fluids to perform a specific interaction (e.g., the detection of a particular marker for a disease condition) are also contemplated. Furthermore, devices may even include stored reagents in a particular sequence. For example, in one embodiment, the application of a predetermined, non-zero pressure differential between the inlet and outlet of the device can allow the reagents, which may be stored as plugs of fluids in the device prior to first use, to flow in a particular sequence through an analysis region for a predetermined amount of time to allow pre-washing, interaction of components, and post-interaction steps to occur. The velocity at which these fluids flow through the analysis region can be controlled by the use of flow constriction regions and other embodiments described herein. Additional examples are described below.

Figure 4:
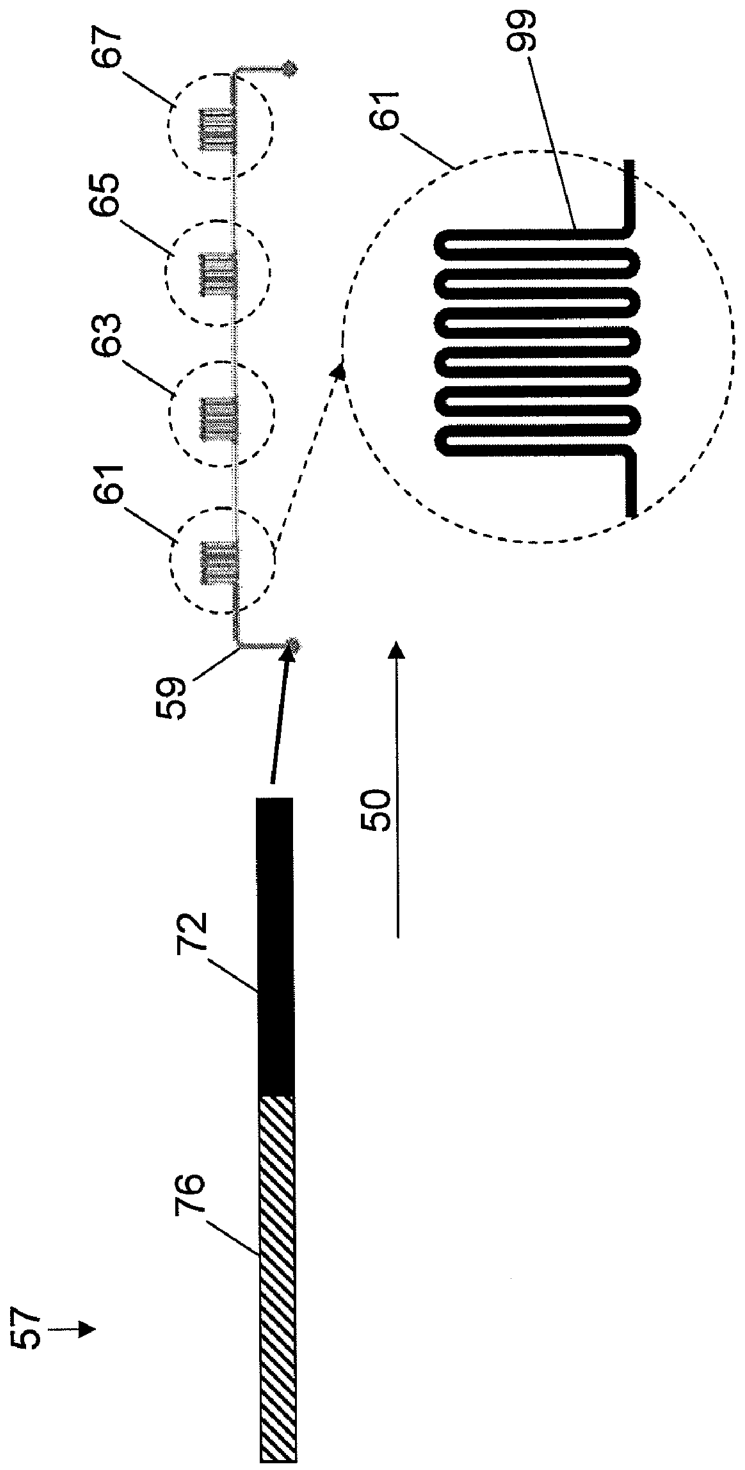
FIG. 4 shows an example of a device that can be used to perform an assay according to one embodiment of the invention.

FIG. 4 shows an example of a device that includes a flow constriction region and which can be used to perform an assay. As shown in the embodiment illustrated in FIG. 4, microfluidic system 57 includes microfluidic channel 59 in fluid communication with four analysis regions 61, 63, 65 and 67 positioned in series. One or more flow constriction regions can be positioned before, after, on either side of, or between the analysis regions. As illustrated, each analysis region is in the form of a meandering (serpentine) channel 99, which is described in more detail in International Patent Publication No. WO2006/113727 (International Patent Application Serial No. PCT/US06/14583), filed Apr. 19, 2006 and entitled "Fluidic Structures Including Meandering and Wide Channels," which is incorporated herein by reference in its entirety for all purposes. In one embodiment, a first fluid 72 (e.g., a test fluid, such as a sample containing a component to be reacted or analyzed) is flowed into microfluidic channel 59 and each of the analysis regions. Fluid 72 may contain a component that interacts with a component positioned at one or more analysis regions. For example, the surfaces of the analysis regions may be pre-fabricated with physisorbed molecules to perform a particular assay.

In one embodiment, an immunoassay can be performed by patterning analysis region 61 with Tween, analysis regions 63 and 65 with anti-human IgG, and analysis region 67 with human IgG. In this embodiment, the immunoassay is designed to detect total human IgG in whole blood. Thus, the introduction of fluid 72 (e.g., whole blood) into the microfluidic system can cause binding between components of one or more analysis regions with a component of the sample. The velocity of fluid 72, and therefore, the amount of time that fluid 72 resides in the analysis regions, can be controlled using one or more flow constriction regions of the microfluidic system. For example, second fluid 76 may be a high viscosity fluid that, when flowed into the flow constriction region, causes fluid 72 to slow down. This can allow additional time for the components of fluid 72 to interact with components disposed in the analysis regions. As described herein, the volume and viscosities of fluids 72 and 76, and the dimensions of the flow constriction region(s) can be predetermined and pre-calculated to allow fluid 72 to remain in the analysis regions for a predetermined amount of time, even while a constant pressure drop is applied between an inlet and an outlet of the device. After the sample has flowed over the analysis regions, additional reagents such as amplification reagents and buffer solutions can then be flowed over the analysis regions.

In one particular embodiment, a device including a flow constriction region is used for performing an immunoassay for human IgG and uses sliver enhancement for signal amplification. The device shown in FIG. 4, a device having a similar configuration as those described in U.S. Patent Apl. Ser. No. 60/927,640, filed May 4, 2007, and U.S. patent application Ser. No. 12/113,503, filed May 1, 2008, entitled "Fluidic Connectors and Microfluidic Systems", which is incorporated herein by reference its entirety for all purposes, or a different device may be used to perform the immunoassay. In such an immunoassay, after delivery of a sample containing human IgG to a reaction area or analysis region, binding between the human IgG and anti-human IgG can take place. One or more reagents, which may be optionally stored in the device prior to use, can then flow over this binding pair complex. One of the stored reagents may include a solution of metal colloid (e.g., a gold conjugated antibody) that specifically binds to the antigen to be detected (e.g., human IgG). This metal colloid can provide a catalytic surface for the deposition of an opaque material, such as a layer of metal (e.g., silver), on a surface of the analysis region. The layer of metal can be formed by using a two component system: a metal precursor (e.g., a solution of silver salts) and a reducing agent (e.g., hydroquinone), which can optionally be stored in different channels prior to use.

As a positive or negative pressure differential is applied to the system, the silver salt and hydroquinone solutions can merge at a channel intersection, where they mix (e.g., due to diffusion) in a channel, and then flow over the analysis region. Therefore, if antibody-antigen binding occurs in the analysis region, the flowing of the metal precursor solution through the region can result in the formation of an opaque layer, such as a silver layer, due to the presence of the catalytic metal colloid associated with the antibody-antigen complex. The opaque layer may include a substance that interferes with the transmittance of light at one or more wavelengths. Any opaque layer that is formed in the microfluidic channel can be detected optically, for example, by measuring a reduction in light transmittance through a portion of the analysis region (e.g., a meandering channel region) compared to a portion of an area that does not include the antibody or antigen. Alternatively, a signal can be obtained by measuring the variation of light transmittance as a function of time, as the film is being formed in a analysis region. The opaque layer may provide an increase in assay sensitivity when compared to techniques that do not form an opaque layer. Additionally, various amplification chemistries that produce optical signals (e.g., absorbance, fluorescence, glow or flash chemiluminescence, electrochemiluminescence), electrical signals (e.g., resistance or conductivity of metal structures created by an electroless process) or magnetic signals (e.g., magnetic beads) can be used to allow detection of a signal by a detector.

Advantageously, in systems such as those described above, the amount of time that the reagents spend in the analysis region can be controlled by flow constriction regions and other embodiments described herein.

Although immunoassays are primarily described, it should be understood that devices described herein may be used for any suitable chemical and/or biological reaction, and may include, for example, other solid-phase assays that involve affinity reaction between proteins or other biomolecules (e.g., DNA, RNA, carbohydrates), or non-naturally occurring molecules. In some embodiments, a chemical and/or biological reaction involves binding. Different types of binding may take place in devices described herein. The term "binding" refers to the interaction between a corresponding pair of molecules that exhibit mutual affinity or binding capacity, typically specific or non-specific binding or interaction, including biochemical, physiological, and/or pharmaceutical interactions. Biological binding defines a type of interaction that occurs between pairs of molecules including proteins, nucleic acids, glycoproteins, carbohydrates, hormones and the like. Specific examples include antibody/antigen, antibody/hapten, enzyme/substrate, enzyme/inhibitor, enzyme/cofactor, binding protein/substrate, carrier protein/substrate, lectin/carbohydrate, receptor/hormone, receptor/effector, complementary strands of nucleic acid, protein/nucleic acid repressor/inducer, ligand/cell surface receptor, virus/ligand, etc. Binding may also occur between proteins or other components and cells. In addition, devices described herein may be used for other fluid analyses (which may or may not involve binding and/or reactions) such as detection of components, concentration, etc.

In some embodiments, it is desirable to quickly change flow rates of fluids flowing between different regions of a microfluidic system. Quickly changing flow rates is difficult to achieve by some external control systems such as syringe pumps, since some such devices may cause back pressure to build up in the microfluidic system. However, by using systems and methods described herein, high rates of deceleration and/or acceleration can be achieved without the use of valves and/or without externally controlling the system (e.g., changing flow rate by using a syringe pump or other flow-control device).

As described herein, the geometry of the channels of a microfluidic system can be designed to cause an abrupt change in flow rate (e.g., a high rate of acceleration or deceleration) upon a fluid entering or exiting a flow constriction region. For deceleration, a first channel portion may be a non-constriction region and a second channel portion may be a flow constriction region. The most significant change in flow rate may take place upon a relatively high-viscosity fluid first entering the fluid constriction region. Accordingly, the flow rate of a fluid (e.g., a test fluid and/or a relatively high- or low-viscosity fluid) may decrease at a rate of at least 100, 200, 300, 400, 1000, 2000, or 3000 $mL/s^2$ as a result of a fluid (e.g., a relatively high-viscosity fluid) flowing from the first channel portion to the second channel portion, as measured by taking the absolute difference between the flow rates at a first time point just prior to the fluid entering the second channel portion (e.g., when the fluid is flowing in the first channel portion) and a second time point when the flow rate has substantially changed (e.g., decreased by at least 90%) while flowing in the second channel portion, and dividing the difference in the flow rate by the amount of time between the first and second time points. In some cases, the second time point is measured when the fluid has reached a substantially constant flow rate while flowing in the second channel portion (e.g., such that the flow rate within the second channel portion varies by less than 5%). The upper bound for this rate of change may depend on the particular design of the microfluidic system, the volume and viscosity of the fluid(s), the pressure differential between an inlet and an outlet of the system, as well as other factors, and may be less than 10000 $nL/s^2$ in some embodiments.

For acceleration, the first channel portion may be a flow constriction region and the second channel portion may be a non-constriction region. The flow rate of a fluid (e.g., a test fluid and/or a relatively high- or low-viscosity fluid) may increase at a rate of at least 100, 200, 300, 400, 1000, 2000, or 3000 $nL/s^2$ as a result of a fluid (e.g., a relatively high-viscosity fluid) flowing from the first channel portion to the second channel portion, as measured by taking the absolute difference between the flow rate at a first time point just before the fluid exits the first channel portion, and the flow rate at second time point when the fluid has completely exited the first channel portion into the second channel portion. In some such embodiments, the most significant change in flow rate may take place upon the last portion of a relatively high-viscosity fluid exiting the fluid constriction region. Thus, the rate of acceleration may depend on the volume or length of the fluid exiting the first channel portion. To account for this factor, in some cases, the above-mentioned rates may be measured by taking the absolute difference between the flow rate at a first time point just prior to the last portion of the fluid exiting the first channel portion, and the flow rate at a second time point when all of the fluid has exited the first channel portion. In some embodiments, the second time point is measured when the fluid has reached a substantially constant flow rate while flowing in the second channel portion (e.g., such that the flow rate within the second channel portion varies by less than 5%). The upper bound for this rate of change may depend on the particular design of the microfluidic system, the volume and viscosity of the fluid(s), the pressure differential between an inlet and an outlet of the system, as well as other factors, and may be less than 10000 $mL/s^2$ in some embodiments.

A decreased (or increased) flow rate results in a decrease (or increase) in linear velocity, of the fluids in the microfluidic system. The change in linear velocity is the change in flow rate divided by the cross sectional area of the channel. An abrupt change in linear velocity can appear as a virtual stoppage in flow (without actual complete stoppage) or as a sudden start of flow. As examples, the linear velocity of a fluid (e.g., a test fluid and/or a relatively high- or low-viscosity fluid) may decrease (or increase) at a rate of at least 20, 50, 500, 1000, 2000, 5000, 10000, or 15000 $\mu m/s^2$ as a result of a fluid (e.g., a relatively high- or low-viscosity fluid) flowing from a first channel portion to a second channel portion (as measured by one of the methods described herein, e.g., by taking the absolute difference between the flow rates at a first time point just prior to a fluid entering the second channel portion and a second time point when the flow rate has substantially changed by at least 90%, and dividing the difference in the flow rate by the amount of time between the first and second time points). The upper bound for this rate of change may depend on the design of the microfluidic system, the volume and viscosity of the fluid(s), the pressure differential between an inlet and an outlet of the system, as well as other factors, and may be less than 30000 $\mu m/s^2$ in some embodiments.

Changes in flow rate can be measured as a percentage change. This value may be calculated by taking the absolute difference between the flow rates at a first time point just prior to the fluid entering the second channel portion (e.g., when the fluid is flowing in the first channel portion) and a second time point when the flow rate has substantially changed (e.g., decreased by at least 90%), and dividing this value by the flow rate at the first time point to obtain a percentage change. In some cases, the second time point occurs when the fluid has a substantially constant flow rate while in the second channel portion (e.g., such that the flow rate within the second channel portion varies by less than 5%). In some embodiments, relatively high rates of deceleration can result in the flow rate of one or more fluids decreasing quickly to nearly a stop (e.g., an at least 90%, 95%, or 97% reduction, but less than a 100% reduction in flow rate). For example, a relatively viscous fluid may have a first flow rate at a first time point just prior to the relatively viscous fluid entering a fluid constriction region. The amount of time between the first time point and a second time point where the fluid has an at least 90% reduction (or, in some cases, at least 95% reduction) in flow rate (but less than a 100% reduction in flow rate) relative to the first flow rate may be less than 10 seconds, less than 5 seconds, less than 3 seconds, less than 2 seconds, or less than 1 second. In some embodiments, the at least 90% (or 95%) reduction in flow rate may be determined when the flow rate of the fluid reaches this value and is substantially constant (e.g., varying by less than 10% or 5%). Similarly, accelerations can be measured as the percentage acceleration as the ratio of the initial flow rate and the final flow rate. Accelerations of at least 99% can be achieved in 3 seconds in some embodiments.

Percentage change in flow rate can be divided by the amount of time between the first and second time points to get another measure of change. For example, a 95% change in flow rate in 1 second would result in a 95%/s change; in 2 seconds it would be 47.5%/s. Decelerations and accelerations of at least 3%/s, 5%/s, 10%/s, 15%/s 20%/s, 30%/s, 48%/s, 70%/s, 80%/s, 100%/s, and even 200%/s are possible, in certain embodiments, as the result of a fluid flowing from one channel portion to another channel portion.

Another useful measure of change in flow is as a ratio of the faster flow to the slower flow. For example, a 90% reduction in flow calculated in the manner described above corresponds to a 10 fold reduction in flow (and 95% corresponding to 20 fold, 99% corresponding to 100 fold). As shown in equation 2, this ratio should match the ratio of the higher viscosity fluid to that of the lower viscosity fluid. Calculations involving flow rate increases and decreases are presented in the Examples section.

As described herein, such high rates of deceleration and/or acceleration can be achieved using one or more fluid constrictions and relatively high- or low-viscosity fluids in combination with the description herein, and in some cases, without the need for or use of moving parts (e.g., valves) or external control (e.g., changing flow rate by using pumps or vacuums that vary pressure).

High rates of deceleration and/or acceleration of fluids are useful for precisely controlling the volume and/or amount of time a fluid is in contact with a particular region of a microfluidic system. In addition, high rates of deceleration and/or acceleration can prevent or reduce cross-contamination of fluids. For example, as mentioned above, in some embodiments it is not desirable to flow fluids at high velocities over a surface of an analysis region after performance of a chemical and/or biological reaction, since doing so would wash away any signal that has been built up within the region. For instance, referring to FIG. 4, if different component interactions occurred at analysis regions 61, 63, 65, and 67, one way of reducing or preventing cross-flow of the components from one analysis region to another is by substantially reducing the fluid flow in the system after the interactions have occurred. This can reduce the flow of components from an upstream analysis region (e.g., analysis region 61, 63 and/or 65) to a downstream analysis region, thereby allowing the signal at each analysis region to be preserved without contamination.

For instance, the decrease of flow rate of the fluids may essentially prevent transport of a component from one analysis region to another during measurement of a signal from one or more analysis regions. In addition, the analysis regions may be sufficiently separated from each other such that the time it takes to measure a signal is less than the time for diffusion of components from one analysis region to another. Advantageously, this reduction or prevention of cross-flow between components can take place using viscous fluids and flow constriction regions, even while a constant non-zero pressure drop is applied between an inlet and an outlet of the microfluidic system. Therefore, fluid valves and/or externally varying flow rate by using syringe pumps or other flow-control devices are not required.

Fully stopping or substantially stopping fluid flow are examples of velocity control. In some embodiments, a fluid having a high viscosity can be used in a microfluidic system described herein to slow down one or more fluids such that the effect is a virtual stop in flow. There are many instances where stopping or substantially slowing down flow is important. One example is safety when performing chemical or biological assays. In some such systems, it may be desirable to ensure that reagents do not enter or exit a certain section of a microfluidic system. For example, if hazardous reagents are used, a safety feature of the device may include a flow constriction region positioned near an outlet such that the reagents do not exit the device. Additional examples are described in more detail below.

Figure 5A:
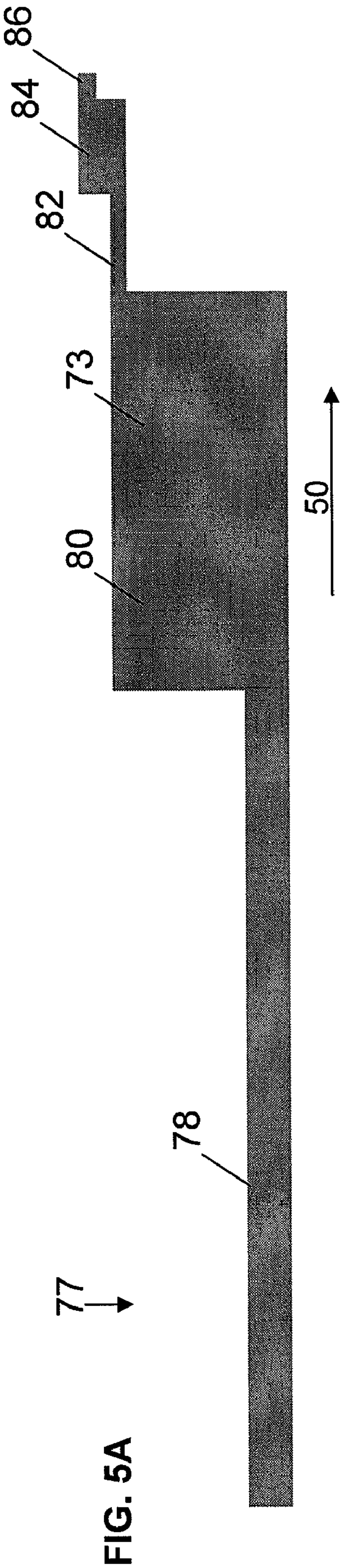
FIGS. 5A-5C show flow of a fluid in a microfluidic system comprising a liquid containment region according to one embodiment of the invention.
Figure 5B:
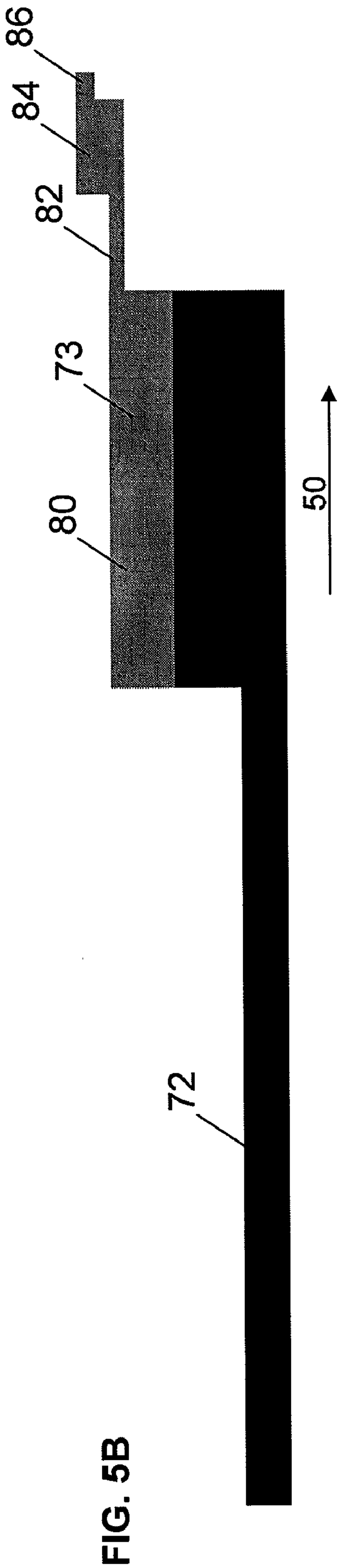
Figure 5C:
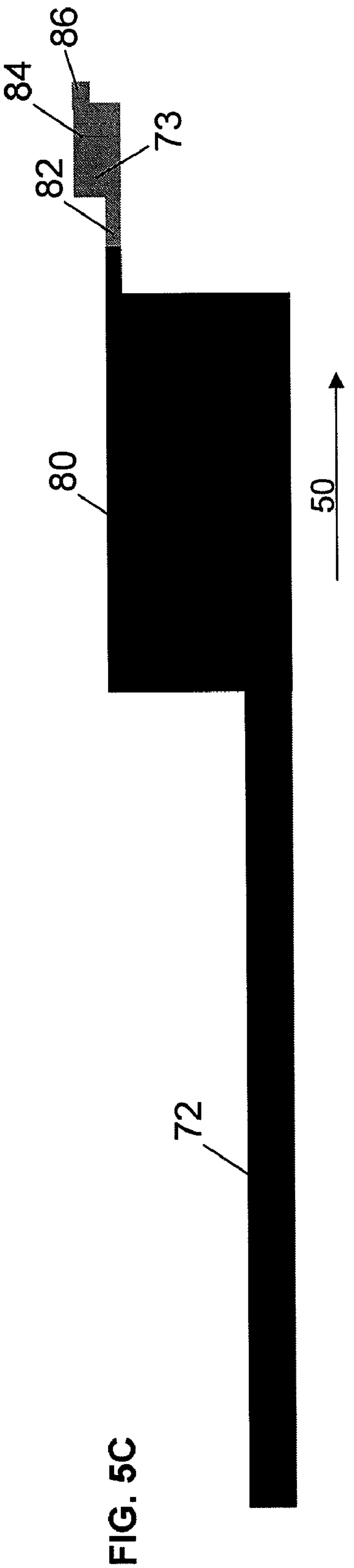

As shown in the embodiments illustrated in FIGS. 5A-5C, microfluidic system 77 may include a microfluidic channel 78 in fluid communication with a liquid containment region 80. Downstream of the liquid containment region is a flow constriction region 82 in fluid communication with an overflow region 84. The overflow region is connected to an outlet 86. An analysis region (not shown) may be positioned upstream of the liquid containment region.

The liquid containment region may be used as a region to capture one or more liquids flowing in the device, while allowing gases or other fluids in the device to pass through the region. This may be achieved, in some embodiments, by positioning one or more absorbent materials in the liquid containment region for absorbing the liquids. In some cases, the liquid containment region prevents any liquid from passing through the region, thereby preventing any liquid from exiting the device. The liquid containment region may be in the form of a reservoir, channel, or any other suitable configuration as described below and in U.S. Patent Apl. Ser. No. 60/994,412, filed Sep. 19, 2007, and U.S. patent application Ser. No. 12/196,392, filed Aug. 22, 2008, entitled "Liquid containment for integrated assays", which is incorporated herein by reference in its entirety for all purposes.

As shown in the embodiment illustrated in FIG. 5B, a fluid 72 may flow into the liquid containment region, e.g., after an assay or another analysis has been performed upstream of this portion of the device. In some embodiments, the volume of the liquid containment region is designed such that it is larger than the volume of fluid intended to be flowed in the microfluidic system. Accordingly, all or most of the fluids (e.g., liquids) flowing in the microfluidic system may be captured by the liquid containment region. However, in some cases, a small portion of a fluid may exit the liquid containment region. Because flow constriction region 82 is positioned downstream of the liquid containment region, the introduction of a fluid into the flow constriction region can drastically decrease the flow rate of the fluids flowing in the microfluidic system. In some embodiments, the cross-sectional area of the flow constriction region can be so small so that any liquid, whether it be a relatively high viscosity fluid or a relatively low viscosity fluid, causes a substantial decrease in flow rate once the fluid enters this region. For example, a cross-sectional area of a flow constriction region may be less than 250 $\mu m^2$, less than 150 $\mu m^2$, less than 100 $\mu m^2$, less than 75 $\mu m^2$, less than 50 $\mu m^2$, less than 25 $\mu m^2$, less than 10 $\mu m^2$, less than 5 $\mu m^2$, or less than 1 $\mu m^2$.

In one particular embodiment, a vacuum is positioned at outlet 86, and is used to cause fluid 72 (e.g., in the form of a liquid) and a fluid 73 (e.g., in the form of air) to flow in the microfluidic system. The flow rate of the fluids remain high as long as air flows through the flow constriction region, as illustrated in FIG. 5B. However, as is illustrated in FIG. 5C, once liquid 72 fills the liquid containment region and reaches flow constriction region 82, the flow rate decreases considerably, even if a constant pressure drop is being applied. If the flow constriction region is sized appropriately, the flow rate decreases enough to approximate stoppage, without actually stopping fluid flow. Thus, there is no need for immediate stoppage of the vacuum, and yet no liquid exits the system.

Any fluid that may flow past the flow constriction region may be contained in overflow region 84. Thus, in one method of operating a microfluidic system, no compressible fluids (e.g., liquids) exit an outlet of the device during use. This mechanism can keep potentially infectious or other hazardous fluids contained in a microfluidic system, and may be useful for disposable microfluidic cassettes.

Figures 6A, 6B, 6C:
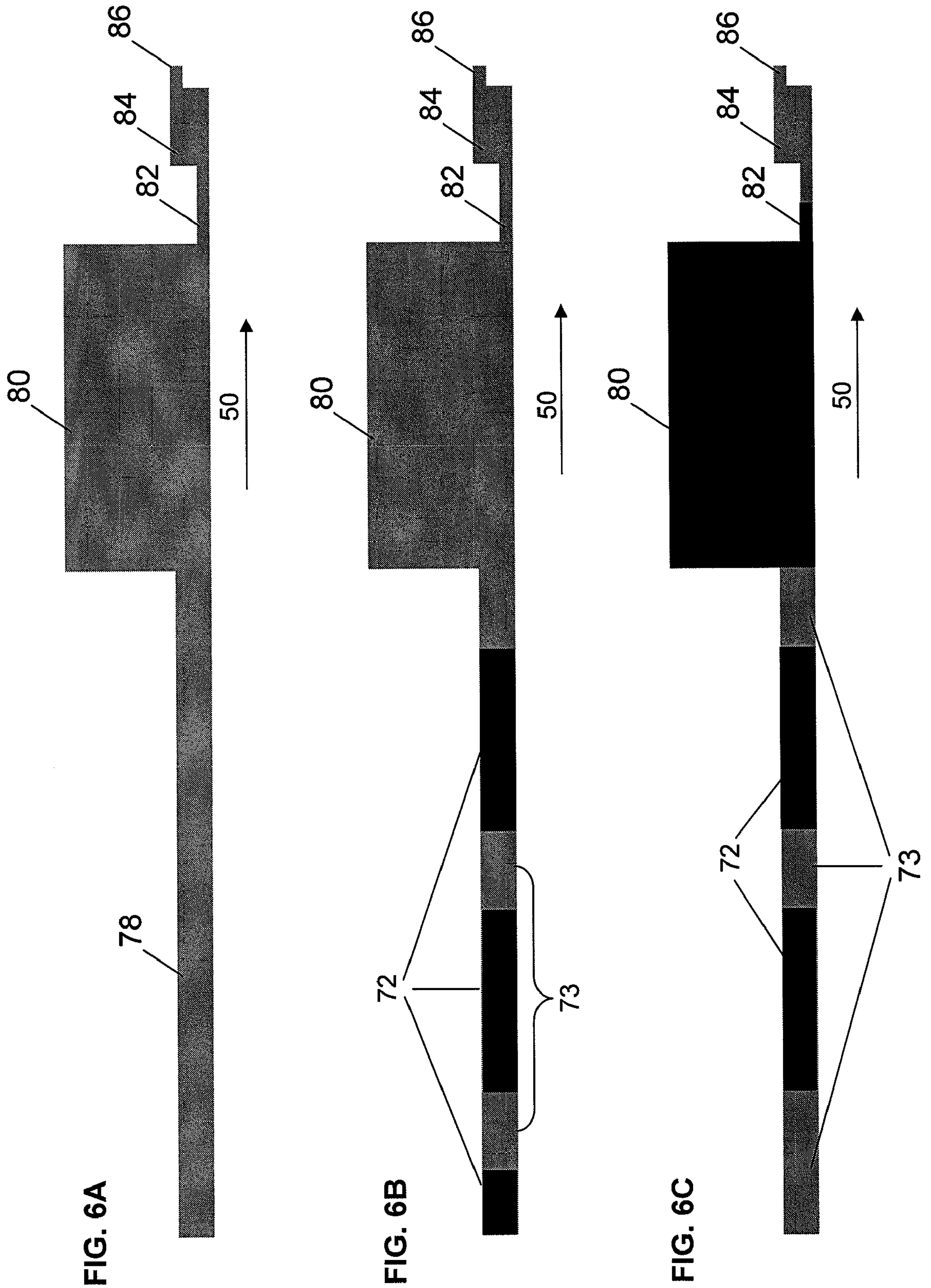
FIGS. 6A-6C show the flow of plugs of fluid flowing in a microfluidic system comprising a liquid containment region according to one embodiment of the invention.

As shown in the embodiment illustrated in FIGS. 6A-6C, methods of operating a microfluidic system may include the use of plugs of fluid 72 (e.g., a liquid) interspersed with plugs of a second fluid 73 (e.g., a compressible fluid such as air). The plugs of liquid may be captured in liquid containment region 80, while the plugs of air can flow through the liquid containment region at a relatively high flow rate. If the liquid containment region eventually fills with the liquid, the liquid may enter the constriction region, thereby slowing the flow rate of the fluids upstream of the flow constriction region. In some cases, the microfluidic system can be designed (e.g., with the use of a valve or an impediment) such that the entrance of a fluid in a flow constriction region stops the flow of fluids. In other embodiments, however, the flow rate of the fluids are substantially reduced, but not stopped. In either case, the flow constriction region may prevent any of the fluid in the microfluidic system from exiting via the outlet during operation as a result of the decrease in flow rate of the fluid.

Figures 7A, 7B, 7C:
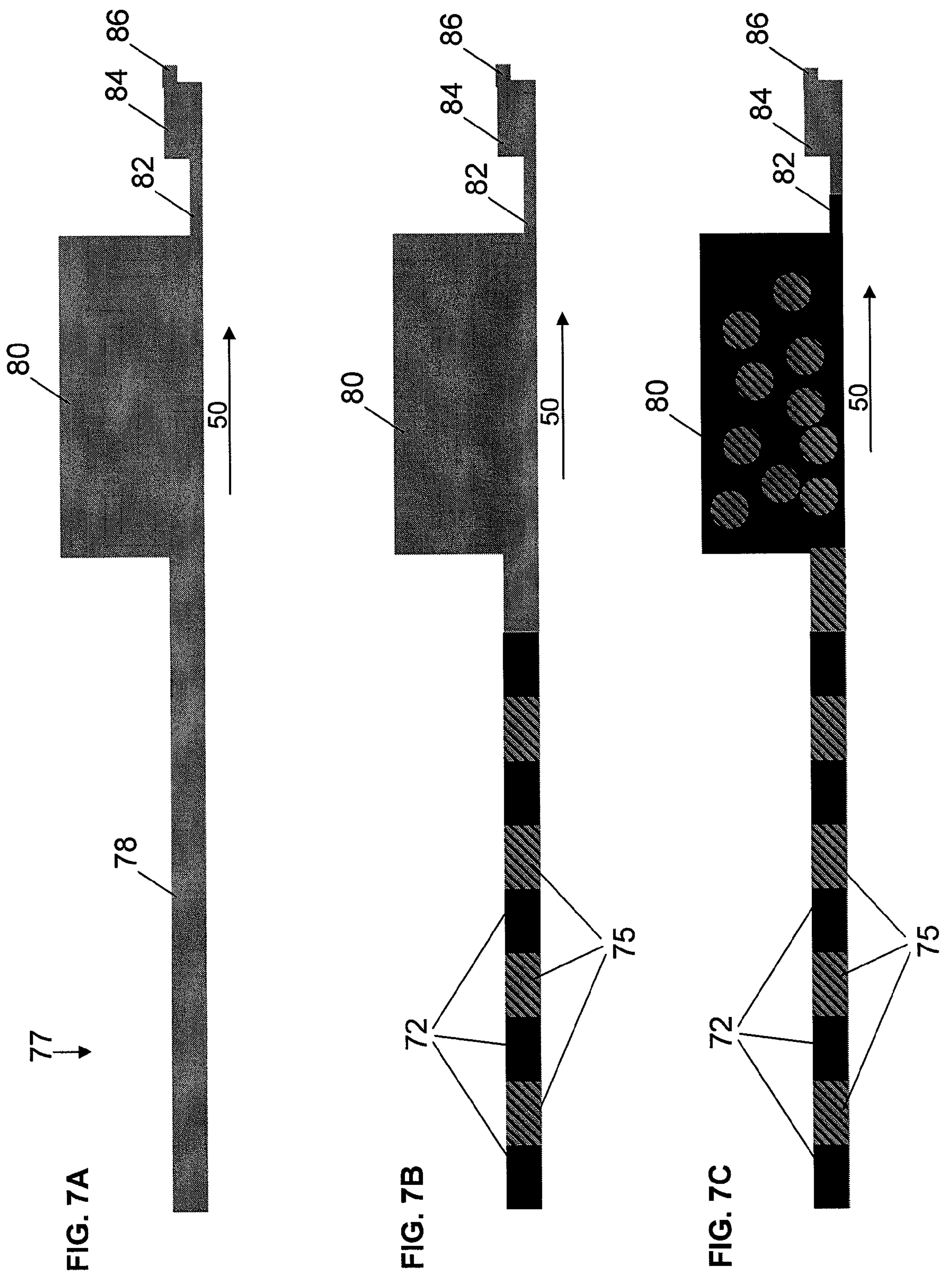
FIGS. 7A-7C show the flow immiscible fluids in the form of plugs in a microfluidic system comprising a liquid containment region according to one embodiment of the invention.

FIGS. 7A-7C show another variation of microfluidic system 77 in which two different fluids are captured in liquid containment region 80. As illustrated, first fluid 72 (e.g., an aqueous solution) and second fluid 75 (e.g., a hydrophobic solution) may be immiscible, and either fluid entering flow constriction region 82 may cause fluids upstream of this region to slow down or be prevented from exiting the device.

Figures 8A, 8B, 8C:
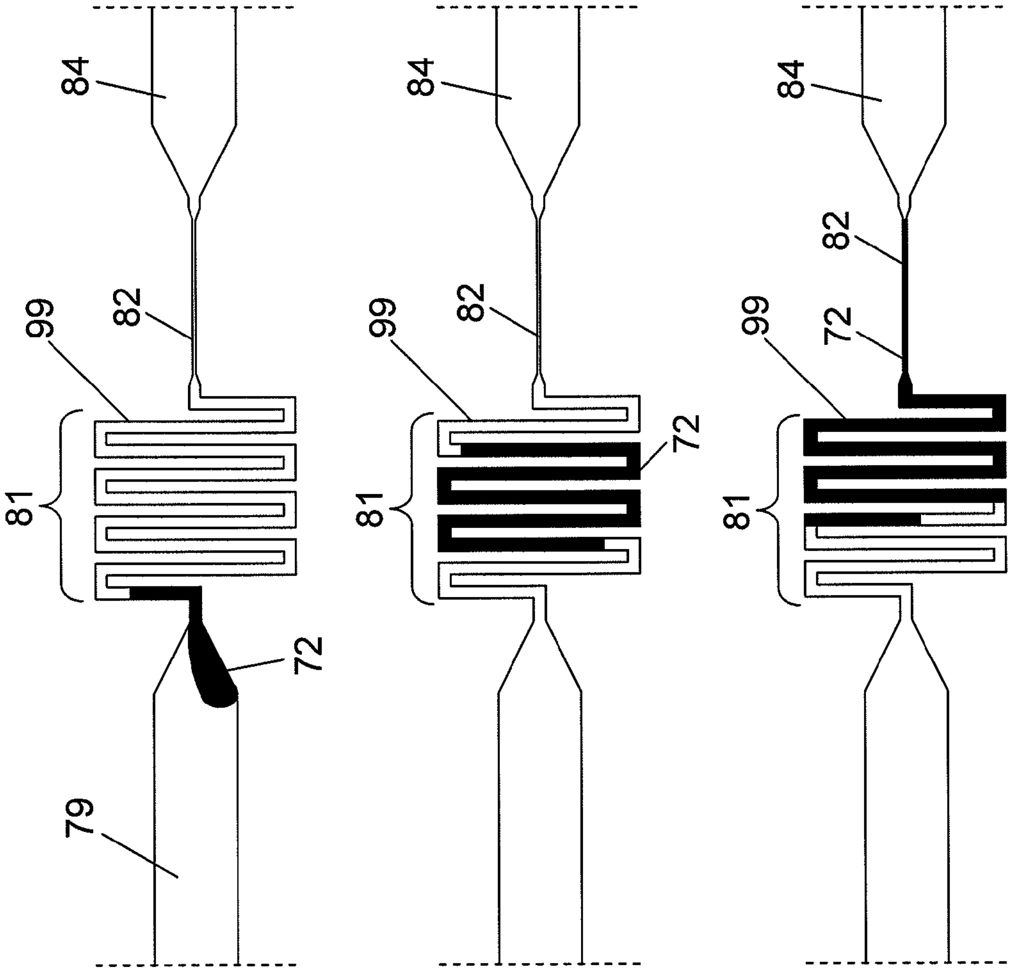
FIGS. 8A-8C show a flow constriction region associated with a detection region near an outlet of a microfluidic system according to one embodiment of the invention.

In some embodiments, a flow constriction region is associated with a detector that can detect the presence or absence of a fluid in or near the flow constriction region. For example, as shown in embodiments illustrated in FIGS. 8A-8C, a microfluidic system includes a detection region 81 in the form of a meandering channel positioned adjacent a microfluidic channel 79. As a result of the meandering channel of the detection region having a smaller cross-sectional area than that of channel 79, fluid 72 entering the meandering channel can cause fluids upstream of this section to slow down. Furthermore, a detector (not shown) may be aligned with detection region 81 to detect the presence of a fluid in this region. Upon detection of any liquid (or a particular type of liquid) in detection region 81, a signal may be sent to a control system (not shown), which can shut down or modulate a source of fluid flow in the system (e.g., a source of vacuum or a pump), thereby preventing the liquid from exiting the device. Additionally or alternatively, a second fluid constriction region 82 may be positioned adjacent the meandering channel and may be used to reduce the flow rate of fluids even more if fluid 72 exits the meandering channel. These features may be combined with one or more fluid containment regions in some devices.

Some embodiments of the invention are in the form of a kit that may include, for example, a microfluidic system, a source for promoting fluid flow (e.g., a vacuum), and/or one, several, or all the reagents necessary to perform an analysis except for the sample to be tested. In some embodiments, the microfluidic system of the kit may have a configuration similar to one or more of those shown in FIGS. 1-8 and/or as described herein.

The kit may include reagents and/or fluids that may be provided in any suitable form, for example, as liquid solutions or as dried powders. In some embodiments, a reagent is stored in the microfluidic system prior to first use, as described in more detail below. When the reagents are provided as a dry powder, the reagent may be reconstituted by the addition of a suitable solvent, which may also be provided. In embodiments where liquid forms of the reagent are provided, the liquid form may be concentrated or ready to use. The fluids may be provided as specific volumes (or may include instructions for forming solutions having a specific volume) to be flowed in the microfluidic system. One or more fluids may be, for example, a relatively low viscosity fluid that can be used to control the flow rate of fluids in the system. One or more relatively high viscosity fluids may be included for a similar purpose. For instance, in some embodiments, the kit may include a microfluidic system and a known volume of a relatively high viscosity fluid such that when the high viscosity fluid flows from one channel portion to another, the flow rate of one or more fluids in the system decreases by a predetermined and pre-calculated amount. The components may be chosen to cause a decrease/increase in flow rate by any suitable amount (e.g., by a factor of at least 50) compared to the absence of flowing of the fluid from the one channel portion to the other.

The kit may be designed to perform a particular analysis such as the determination of a specific disease condition. In order to perform a particular analysis or test using the kit, the microfluidic system may be designed to have certain geometries, and the particular compositions, volumes, and viscosities of fluids may be chosen so as to provide optimal conditions for performing the analysis in the system. For example, if a reaction to be performed at an analysis region requires the flow of an amplification reagent over the analysis region for a specific, pre-calculated amount of time in order produce an optimal signal, the microfluidic system may be designed to include a flow constriction region having a particular cross-sectional area and length to be used with a fluid of specific volume and viscosity in order to regulate fluid flow in a predetermined and pre-calculated manner. Furthermore, the kit may include a device or component for promoting fluid flow, such as a source of vacuum dimensioned to be connected to an outlet. The device or component may include one or more pre-set values so as to create a known (and optionally constant) pressure drop between an inlet and an outlet of the microfluidic system. Thus, the kit can allow one or more reagents to flow for a known, pre-calculated amount of time at the analysis region, or at other regions of the system, during use. Those of ordinary skill in the art can calculate and determine the parameters necessary to regulate fluid flow using general knowledge in the art in combination with equations 1-4 and the description provided herein.

A kit described herein may further include a set of instructions for use of the kit. The instructions can define a component of instructional utility (e.g., directions, guides, warnings, labels, notes, FAQs ("frequently asked questions"), etc., and typically involve written instructions on or associated with the components and/or with the packaging of the components for use of the microfluidic system. Instructions can also include instructional communications in any form (e.g., oral, electronic, digital, optical, visual, etc.), provided in any manner such that a user will clearly recognize that the instructions are to be associated with the components of the kit.

As mentioned above, in some embodiments, microfluidic systems described herein contain stored reagents prior to first use of the device and/or prior to introduction of a sample into the device. In some cases, one or both of liquid and dry reagents may be stored on a single microfluidic substrate. Additionally or alternatively, the reagents may also be stored in separate vessels such that a reagent is not in fluid communication with the microfluidic system prior to first use. The use of stored reagents can simplify use of the microfluidic system by a user, since this minimizes the number of steps the user has to perform in order to operate the device. This simplicity can allow microfluidic systems described herein to be used by untrained users, such as those in point-of-care settings, and in particular, for devices designed to perform immunoassays. It has been demonstrated previously that the storage of the reagents in the form of liquid plugs separated by air gaps were stable for extended periods of time (see, for example, International Patent Publication No. WO2005/072858 (International Patent Application Serial No. PCT/US2005/003514), filed Jan. 26, 2005 and entitled "Fluid Delivery System and Method," which his incorporated herein by reference in its entirety for all purposes). In other embodiments, however, microfluidic devices described herein do not contain stored reagents prior to first use of the device and/or prior to introduction of a sample into the device.

As used herein, "prior to first use" of the device means a time or times before the device is first used by an intended user after commercial sale. First use may include any step(s) requiring manipulation of the device by a user. For example, first use may involve one or more steps such as puncturing a sealed inlet to introduce a reagent into the device, connecting two or more channels to cause fluid communication between the channels, preparation of the device (e.g., loading of reagents into the device) before analysis of a sample, loading of a sample onto the device, preparation of a sample in a region of the device, performing a reaction with a sample, detection of a sample, etc. First use, in this context, does not include manufacture or other preparatory or quality control steps taken by the manufacturer of the device. Those of ordinary skill in the art are well aware of the meaning of first use in this context, and will be able easily to determine whether a device of the invention has or has not experienced first use. In one set of embodiments, devices of the invention are disposable after first use, and it is particularly evident when such devices are first used, because it is typically impractical to use the devices at all after first use.

As described herein, a microfluidic system may optionally include one or more liquid containment region(s) that may be used to capture one or more liquids flowing in the device. Such a microfluidic system may also include a source of vacuum positioned at an outlet of the device. In some embodiments where an absorbent material is positioned in a liquid containment region that is separated from an outlet (e.g., by a microfluidic channel), the absorbent material is not in direct contact with an atmosphere external to the device. In some such embodiments, the absorbent material is not accessible via the outlet. This arrangement may, in some cases, reduce or prevent evaporation of a liquid from the absorbent material and/or reduce exposure of the liquid to a user. Sometimes, this arrangement can be combined with a means of fluid flow other than absorption such as application of positive pressure at an inlet, application of vacuum at an outlet, gravity, capillary forces, or combinations thereof. In certain embodiments, an external source such as application of a positive pressure or a vacuum can be used to control fluid flow, instead of forces that are inherent to a material and/or a dimension of a device (such as wicking and capillary forces). Thus, the absorbent material, in some such embodiments, is not used as a wick for controlling or modulating fluid flow in the device. In other words, the act of absorbing does not substantially modulate the flow rate of a liquid flowing at a region positioned upstream or downstream of the liquid containment region and/or at a region positioned outside of an analysis region. The act of absorbing does not substantially modulate the flow rate of a fluid if, for example, the rate of flow of the fluid is constantly being controlled by a source other than absorption (e.g., pumping, gravity, capillary action, source of vacuum, etc.). If any absorption is present in the microfluidic system (e.g., in a liquid containment region), the resulting flow rate as provided by the source may be much greater than the rate of absorption.

In certain embodiments, the flow rate as provided by a non-wicking source may be at least 10 times, at least 20 times, at least 50 times, at least 70 times, or at least 100 times greater than the flow rate provided by the wicking source, all else being equal. Therefore, even though absorption may take place in a microfluidic system, absorption does not substantially contribute to the rate of fluid flow. Accordingly, in some embodiments, the volumetric flow rate of a fluid in the microfluidic system is not substantially altered due to absorption. In certain such embodiments, because the flow rate of the fluid is not substantially modulated due to absorption, a liquid containment region and absorbent material associated therewith, if present, may be configured in a variety of configurations and arrangements without needing to account for the size and dimensions of the absorbent material. This method of operating the device affords flexibility in the design and use of the device.

In other embodiments, however, fluid flow in the device may be controlled and/or modulated by wicking action by using the absorbent material as the main source of driving fluid flow. Control and/or modulation of fluid flow can be enhanced especially in embodiments where the absorbent material is contained in a liquid containment region having an outlet as part of the liquid containment region (e.g., where the absorbent material is in direct contact with an atmosphere external to the device via the outlet), since liquid can evaporate from the absorbent material, thereby enhancing the wicking action. In certain such embodiments, the absorbent material may extend beyond the microfluidic system, e.g., by protruding out of an outlet. Fluid flow in the device may also be controlled and/or modulated by wicking action without substantial evaporation by, for example, not letting the absorbent material extend beyond the microfluidic system but while using the absorbent material as the main source of driving fluid flow.

As mentioned above, in some instances, a liquid containment region is configured and arranged to contain, absorb or capture substantially all of the liquid in a device, thereby preventing any liquid from exiting the device. That is, substantially all of the liquid introduced and/or stored in a microfluidic system ends up in the liquid containment region after use of the device. This arrangement can reduce the chances of a user being exposed to and/or infected by a liquid contained in the device. In some such embodiments, the liquid containment region further includes a disinfectant material that neutralizes, reacts with, denatures, disinfects, and/or sterilizes a liquid, a component of the liquid, or a portion of a microfluidic system in contact with the liquid, as described in more detail below. Substantially all of the liquid may include, for example, greater than 95% of any liquid in the microfluidic system in one embodiment, or, in other embodiments, greater than 97%, greater than 99%, or greater than 99.9% of any liquid in the microfluidic system. Any remaining liquid that is not captured by the system may include, for example, minute portions of the liquid that may be associated with a binding reaction at a reaction site and/or any liquid remaining in a valve or other component positioned in the device (e.g., droplets or films of liquid left on a surface of the microfluidic channel).

In some cases, the volume of the liquid containment region and/or volume of the absorbent material is designed to be greater than the amount of liquid to be used with the device (e.g., stored, introduced, etc.). For instance, in some embodiments, the total volume of liquids introduced into the device, stored in the device, and/or flowing in the device is less than the volume of the liquid containment region. In some such embodiments, substantially all of the liquid introduced, stored, and/or flowed in the device can be absorbed in the liquid containment region. In another embodiment, the combined volume of the microfluidic channels, inlets, and other areas of the device besides the liquid containment region is less than the volume of the liquid containment region and/or the volume of the absorbent material.

A variety of absorbent materials may be used in devices described herein. The material and configuration of the absorbent material may depend, at least in part, on the fluid to be absorbed, compatibility with material(s) used to form the microfluidic system, configuration of the liquid containment region, or other factors. The absorbent material may be, for example, a solid material, a porous material, or in the form of particles, a powder, or a gel. In certain embodiments, the absorbent material is dried such as a piece of fabric, cellulose (e.g., paper), cotton, or the like. The absorbent material may include a polymer such poly(dimethylsiloxane), polypropylene, polyacrylamide, agarose, polyvinylidene fluoride, ethylene-vinyl acetate, styrenes, polytetrafluoro ethylene, polysulfones, polycarbonates, and dextran. In certain embodiments, the absorbent material is in the form of a single layer of material, multiple layers of materials, particles, beads, a coating, or a film. The absorbent material may be hydrophilic, hydrophobic, or a combination thereof. In some embodiments, a liquid containment region can include more than one types of absorbent material contained therein.

A variety of determination (e.g., measuring, quantifying, detecting, and qualifying) techniques may be used. Determination techniques may include optically-based techniques such as light transmission, light absorbance, light scattering, light reflection and visual techniques. Determination techniques may also include luminescence techniques such as photoluminescence (e.g., fluorescence), chemiluminescence, bioluminescence, and/or electrochemiluminescence. Those of ordinary skill in the art know how to modify microfluidic devices in accordance with the determination technique used. For instance, for devices including chemiluminescent species used for determination, an opaque and/or dark background may be preferred. For determination using metal colloids, a transparent background may be preferred. Furthermore, any suitable detector may be used with devices described herein. For example, simplified optical detectors, as well as conventional spectrophotometers and optical readers (e.g., 96-well plate readers) can be used.

In some embodiments, determination techniques may measure conductivity. For example, microelectrodes placed at opposite ends of a portion of a microfluidic channel may be used to measure the deposition of a conductive material, for example an electrolessly deposited metal. As a greater number of individual particles of metal grow and contact each other, conductivity may increase and provide an indication of the amount of conductor material, e.g., metal, that has been deposited on the portion. Therefore, conductivity or resistance may be used as a quantitative measure of analyte concentration.

Another analytical technique may include measuring a changing concentration of a precursor from the time the precursor enters the microfluidic channel until the time the precursor exits the channel. For example, if a silver salt solution is used (e.g., nitrate, lactate, citrate or acetate), a silver-sensitive electrode may be capable of measuring a loss in silver concentration due to the deposition of silver in a channel as the precursor passes through the channel.

When more than one chemical and/or biological reaction (e.g., a multiplex assay) is performed on a device, the signal acquisition can be carried out by moving a detector over each analysis region. In an alternative approach, a single detector can detect signal(s) in each of the analysis regions simultaneously. In another embodiment, an analyzer can include, for example, a number of parallel optical sensors/detectors, each aligned with a analysis region and connected to the electronics of a reader. Additional examples of detectors and detection methods are described in more detail in U.S. Patent Apl. Ser. No. 60/994,412, filed Sep. 19, 2007, and U.S. patent application Ser. No. 12/196,392, filed Aug. 22, 2008, entitled "Liquid containment for integrated assays", which is incorporated herein by reference in its entirety for all purposes.

As described herein, a meandering channel of an analysis region may be configured and arranged to align with a detector such that upon alignment, the detector can measure a single signal through more than one adjacent segment of the meandering channel. In some embodiments, the detector is able to detect a signal within at least a portion of the area of the meandering channel and through more than one segment of the meandering channel such that a first portion of the signal, measured from a first segment of the meandering channel, is similar to a second portion of the signal, measured from a second segment of the meandering channel. In such embodiments, because the signal is present as a part of more than one segment of the meandering channel, there is no need for precise alignment between a detector and an analysis region.

The positioning of the detector over the analysis region (e.g., a meandering region) without the need for precision is an advantage, since external (and possibly, expensive) equipment such as microscopes, lenses, and alignment stages are not required (although they may be used in certain embodiments). Instead, alignment can be performed by eye, or by low-cost methods that do not require an alignment step by the user. In one embodiment, a device comprising a meandering region can be placed in a simple holder (e.g., in a cavity having the same shape as the device), and the measurement area can be automatically located in a beam of light of the detector. Possible causes of misalignment caused by, for instance, chip-to-chip variations, the exact location of the chip in the holder, and normal usage of the device, are negligible compared to the dimensions of the measurement area. As a result, the meandering region can stay within the beam of light and detection is not interrupted due to these variations.

Though in some embodiments, systems of the invention may be microfluidic, in certain embodiments, the invention is not limited to microfluidic systems and may relate to other types of fluidic systems. "Microfluidic," as used herein, refers to a device, apparatus or system including at least one fluid channel having a cross-sectional dimension of less than 1 mm, and a ratio of length to largest cross-sectional dimension of at least 3:1. A "microfluidic channel," as used herein, is a channel meeting these criteria.

The "cross-sectional dimension" (e.g., a diameter) of a channel is measured perpendicular to the direction of fluid flow. Some fluidic channels in microfluidic systems described herein have maximum cross-sectional dimensions less than 2 mm, and in some cases, less than 1 mm. In one set of embodiments, all fluid channels containing embodiments of the invention are microfluidic or have a largest cross-sectional dimension of no more than 2 mm or 1 mm. In another set of embodiments, the maximum cross-sectional dimension of the channel(s) containing embodiments of the invention are less than 750 microns, less than 500 microns, less than 200 microns, less than 100 microns, less than 50 microns, less than 25 microns, less than 10 microns, or less than 5 microns. Channels having smaller cross-sectional dimensions may be used as flow constriction regions, for example.

In some cases the dimensions of the channel may be chosen such that fluid is able to freely flow through the article or substrate. The dimensions of the channel may also be chosen, for example, to allow a certain volumetric or linear flowrate of fluid in the channel. Of course, the number of channels and the shape of the channels can be varied by any method known to those of ordinary skill in the art. In some cases, more than one channel or capillary may be used.

A "channel," as used herein, means a feature on or in an article (substrate) that at least partially directs the flow of a fluid. The channel can have any cross-sectional shape (circular, oval, triangular, irregular, square or rectangular, trapezoidal, or the like) and can be covered or uncovered. In embodiments where it is completely covered, at least one portion of the channel can have a cross-section that is completely enclosed, or the entire channel may be completely enclosed along its entire length with the exception of its inlet(s) and outlet(s). A channel may also have an aspect ratio (length to average cross-sectional dimension) of at least 2:1, more typically at least 3:1, 5:1, or 10:1 or more. An open channel generally will include characteristics that facilitate control over fluid transport, e.g., structural characteristics (an elongated indentation) and/or physical or chemical characteristics (hydrophobicity vs. hydrophilicity) or other characteristics that can exert a force (e.g., a containing force) on a fluid. The fluid within the channel may partially or completely fill the channel. In some cases where an open channel is used, the fluid may be held within the channel, for example, using surface tension (e.g., a concave or convex meniscus).

In some embodiments described herein, microfluidic systems include only a single interconnected channel with, for example, less than 5, 4, 3, 2, or 1 channel intersection(s) when in use. A layout based on a single channel with minimal or no intersections may be reliable because there is only one possible flow path for any fluid to travel across the microfluidic chip. In these configurations, the reliability of a chemical and/or biological reaction to be performed in the device is greatly improved compared to designs having many intersections. This improvement occurs because at each intersection (e.g., a 3-way intersection or more), the fluid has the potential to enter the wrong channel. The ability to load a sample without channel intersections can eliminate risk of fluid entering the wrong channel. Because an intersection may represent a risk factor that must be taken into account in product development, controls (either on-chip or based on external inspection) must be set up to insure correct fluid behavior at each interconnection. In certain embodiments described herein, the need for such additional controls can be alleviated.

A microfluidic system described herein may have any suitable volume for carrying out a chemical and/or biological reaction or other process. The entire volume of a microfluidic system includes, for example, any reagent storage areas, reaction areas, liquid containment regions, waste areas, as well as any fluid connectors, and microfluidic channels associated therewith. In some embodiments, small amounts of reagents and samples are used and the entire volume of the microfluidic system is, for example, less than 10 milliliters, less than 5 milliliters, less than 1 milliliter, less than 500 microliters, less than 250 microliters, less than 100 microliters, less than 50 microliters, less than 25 microliters, less than 10 microliters, less than 5 microliters, or less than 1 microliter.

A microfluidic system (e.g., a microfluidic substrate) can be fabricated of any material suitable for forming a microchannel. Non-limiting examples of materials include polymers (e.g., polyethylene, polystyrene, polycarbonate, poly (dimethylsiloxane), and a cyclo-olefin copolymer (COC)), glass, quartz, and silicon. Those of ordinary skill in the art can readily select a suitable material based upon e.g., its rigidity, its inertness to (e.g., freedom from degradation by) a fluid to be passed through it, its robustness at a temperature at which a particular device is to be used, and/or its transparency/ opacity to light (e.g., in the ultraviolet and visible regions). In some embodiments, the material and dimensions (e.g., thickness) of a substrate are chosen such that the substrate is substantially impermeable to water vapor.

In some instances, a microfluidic substrate is comprised of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a channels of the device may be formed in polystyrene or other polymers (e.g., by injection molding) and a biocompatible tape may be used to seal the channels. A variety of methods can be used to seal a microfluidic channel or portions of a channel, including but not limited to, the use of adhesives, gluing, bonding, lamination of materials, or by mechanical methods (e.g., clamping).

The manufacturing processes used to produce devices by injection molding (or other plastic engineering techniques, such as hot embossing), often require molds having non-zero draft angles on some or all of the features to be replicated in plastic. As known to those of ordinary skill in the art, a draft angle is the amount of taper for molded or cast parts perpendicular to the parting line (a square channel with walls perpendicular to the floor having a draft angle of zero degrees). A non-zero draft angle is often necessary to allow demolding of the replica from the molding tool.

The fabrication of microstructures with non-zero draft angles is challenging. For instance, for microfluidic structures (e.g., channels) having various depths, the corresponding mold must have features with multiple heights in addition to non-zero draft angles. These types of moldscan be challenging to fabricate on the microscale, as molding microchannels in plastic with constrictions in draft angle, depth, as well as in width is not trivial.

In fact, few techniques can yield the appropriate shapes for a mold having non-zero draft angles. To widen the breadth of technologies able to produce the appropriate shapes, an indirect route to the fabrication of the mold can be chosen. For instance, the channels themselves can be created in various materials, by various techniques to produce a master. The negative shape of the master is then obtained (e.g., by electrodeposition), resulting in a mold for injection molding. The techniques capable of yielding a master with non-zero draft angles and various depths include: (1) milling with one or more trapezoidal-shaped bits, (2) photolithographic techniques in combination with thick photosensitive polymers, for instance photosensitive glass or photoresist like SU8, in combination with a back-side exposure or a top-side exposure with light with a non-normal angle. An example of the use of non-normal top-side exposure with photosensitive glass to produce features with non-zero draft angles is described in U.S. Pat. No. 4,444,616. The preparation of multiple depths can be achieved by multiple photolithographic exposures onto multiple layers of photosensitive material. (3) KOH etching on silicon substrates can also produce non-zero draft angles, according to the crystalline planes of the silicon. (4) Alternative to straight draft angles, channels having rounded side-walls can also produce suitable master for molds. Such rounded side-walls can be achieved by isotropic etching onto planar surface (e.g., HF etching on Pyrex wafers), or by reflowing structures photoresist by heat treatment.

Accordingly, in some microfluidic systems described herein, it is desirable to have microfluidic components (e.g., channels) having non-zero draft angles. The cross-sections of microfluidic channels having non-zero draft angles may resemble a trapezoid or a parallelogram. The draft angle may be, for example, between 1 and 30 degrees, between 1 and 20 degrees, between 1 and 10 degrees, between 2 and 15 degrees, between 3 and 10 degrees, or between 3 and 8 degrees. In some cases, it is desirable for microfluidic channels to have certain draft angles so that they are compatible with a certain detection technique. For example, in one embodiment, a detection region having a draft angle of more than about 20 degrees is not optimal because it does not allow light from a particular light source to pass through the angled side-walls. Thus, depending on the particular detection technique and components used, microfluidic systems may be fabricated with varying draft angles.

The following examples are intended to illustrate certain embodiments of the present invention, but are not to be construed as limiting and do not exemplify the full scope of the invention.

EXAMPLE 1

Fabrication of Microfluidic Channels

A method for fabricating a microfluidic channel system is described.

Channel systems, such as the ones shown in FIGS. 1-8, were designed with a computer-aided design (CAD) program. The microfluidic devices were formed in poly(dimethylsiloxane) Sylgard 184 (PDMS, Dow Corning, Ellsworth, Germantown, Wis.) by rapid prototyping using masters made in SU8 photoresist (MicroChem, Newton, Mass.). The masters were produced on a silicon wafer and were used to replicate the negative pattern in PDMS. The masters contained two levels of SU8, one level with a thickness (height) of ~70 μm defining the channels in the immunoassay area, and a second thickness (height) of ~360 μm defining the reagent storage and waste areas. Another master was designed with channel having a thickness (height) of 33 μm. The masters were silanized with (tridecafluoro-1,1,2,2-tetrahydrooctyl) trichlorosilane (ABC-R, Germany). PDMS was mixed according to the manufacturer's instructions and poured onto the masters. After polymerization (4 hours, 65° C.), the PDMS replica was peeled off the masters and access ports were punched out of the PDMS using stainless steel tubing with sharpened edges (1.5 mm in diameter). To complete the fluidic network, a flat substrate such as a glass slide, silicon wafer, polystyrene surface, flat slab of PDMS, or an adhesive tape was used as a cover and placed against the PDMS surface. The cover was held in place either by van der Waals forces, or fixed to the microfluidic device using an adhesive.

In other embodiments, the microfluidic channels were made in polystyrene by injection molding. This method is known to those of ordinary skill in the art.

EXAMPLE 2

Regulating Flow Rate Using Differential Viscosity of Fluids and a Flow Constriction Positioned Upstream of an Analysis Region This example describes a method for regulating the flow rate in a microchannel using a flow constriction region positioned upstream of an analysis region and fluids of different viscosities.

The microchannels produced in PDMS or Polystyrene (see Example 1) were sealed against a plate of polystyrene (NUNC Omnitray, VWR, West Chester, Pa.) in the case of PDMS, or a biocompatible adhesive (in the case of polystyrene substrates). For the latter, the polystyrene substrate was drilled to obtain access holes prior to application of the cover. In a different approach, the holes were formed in the thermoplastic during the injection molding process by using pillars inside the cavity of the injection molding machine.

A first channel portion 30 and a third channel portion 38 (e.g., as shown in FIG. 1) were 500 μm wide and 376 μm deep; second channel portion 34, which was used as a flow constriction region, was 120 μm wide and 65 μm deep. All of the microchannels were filled with the following dye solution: blue dye (Erioglancine, Sigma) was prepared at a concentration of 0.5 mg/mL in phosphate buffer saline containing 0.2% Tween 20 (PB S/Tween). With a viscosity of roughly 1 mPa·s, this served as the relatively low viscosity fluid. For a relatively high viscosity fluid, PDMS was used (Fluka, silicone oil DC200, Fluka, 100 mPa·s).

The inlet port of the microfluidic channel was filled with the aqueous dye solution, and a drop of liquid PDMS (~20 μL) was pipetted onto the inlet port of the microchannel. Then a vacuum (−10 kPa) was applied to the outlet of the channel to pull the sequence through the microchannel. Using a stereomicroscope, the velocity of the fluids in the microchannels under vacuum could be monitored by observing the displacement of the interface between the blue dye and the PDMS as a function of time. An initial relatively high linear velocity was observed when only the blue dye flowed through the constriction. A decrease of flow velocity was observed as the PDMS reached and entered the constriction. All flow velocities reported are the linear velocities of flow in the large channel.

Figure 9A:
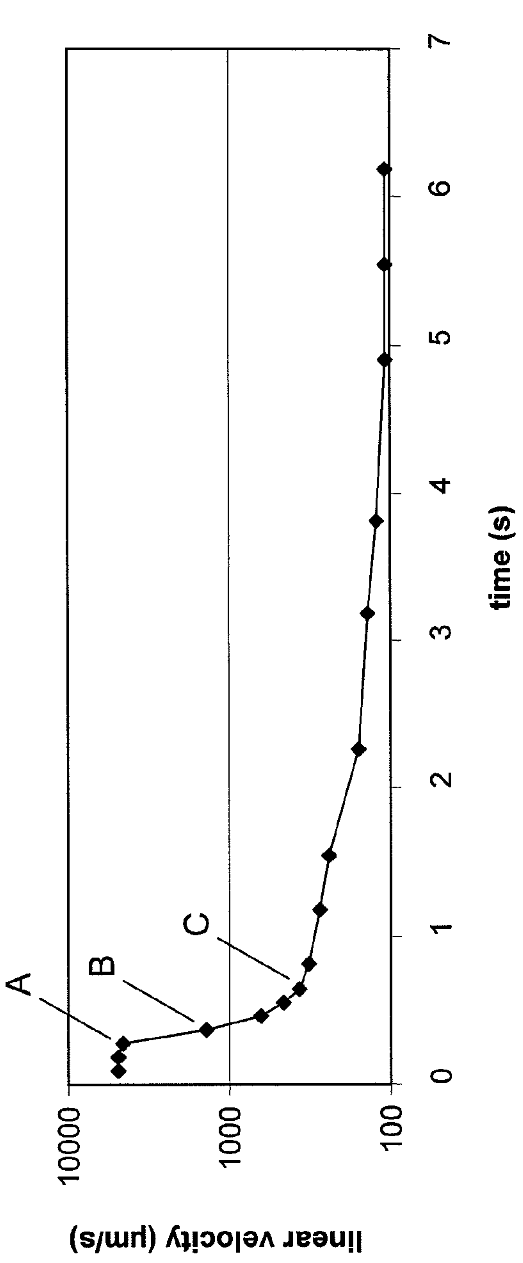
FIGS. 9A and 9B are plots showing deceleration and acceleration of fluids, respectively, in a microfluidic system comprising a flow constriction region positioned upstream of an analysis region according to one embodiment of the invention.

Linear velocity of flow was measured approximately every 0.09 seconds. The initial linear velocity of flow in the non-constriction channel was 4976 μm/s at point A. As shown in FIG. 9A and Table 1A, as soon as the PDMS plug began to enter the flow constriction region (point B), the linear velocity of the plugs and the flow rate dropped by a factor 11 (e.g., from 4976 μm/s to 456 nm/s, and 936 mL/s to 86 mL/s) in 0.45 seconds. This is a deceleration in linear velocity of 10,044 $\mu m/s^2$ and corresponds to a deceleration (in velocity and flow rate) of 91% (relative to the initial flow rate of 4976 μm/s or 936 mL/s), or a deceleration of 202%/s. The deceleration was measured by taking the absolute difference between the flow rate at a first time point just prior to the fluid entering the fluid constriction region (4976 μm/s) and a flow rate at a second time point when it substantially decreased (e.g., by 90%, point C) while flowing in the flow constriction region (456 μm/s). These differences in flow rate were divided by the amount of time between the first and second time points (0.45 s). After 1 second, while the PDMS was still filling the flow constriction region, the flow had decelerated by a factor of 18. After 5 seconds, PDMS filled all of the flow constriction region and the flow was effectively brought to a near, but incomplete stop. With a 100 to 1 ratio of viscosities between the high viscosity fluid and the low viscosity fluid, total deceleration in the range of a factor of 100 was expected. At this minimum flow rate, the flow had decelerated by a factor 47 (e.g., from 4976 μm/s to 106 μm/s, and 936 mL/s to 20 mL/s). This is a deceleration in linear velocity of 974 $\mu m/s^2$, and corresponds to a deceleration (in velocity and flow rate) of 98% (relative to the initial flow rate of 4976 μm/s or 936 mL/s), or a deceleration of 20%/s. This experiment shows that flow rate decreases substantially once a relatively high-viscosity fluid enters a fluid constriction region, as illustrated by the sharp curve between points A and C in FIG. 9A.

TABLE 1A

Deceleration of fluids from a non-constriction region to a flow constriction region

| reference time (s) | V (μm/s) | dV/dt ($\mu m/s^2$) | Q (nL/s) | dQ ($nL/s^2$) | Ratio (fast:slow flow) | Decel. (%) | Decel. (%/s) |
|---|---|---|---|---|---|---|---|
| 0 | 4,976 | | 936 | | | | |
| 0.45 | 456 | 10,044 | 86 | 1,888 | 10.9 | 91% | 202% |
| 1 | 274 | 4,702 | 51 | 884 | 18.2 | 94% | 94% |
| 2 | 160 | 2,408 | 30 | 453 | 31.2 | 97% | 48% |
| 3 | 137 | 1,613 | 26 | 303 | 36.3 | 97% | 32% |
| 4 | 119 | 1,214 | 22 | 228 | 41.8 | 98% | 24% |
| 5 | 106 | 974 | 20 | 183 | 46.7 | 98% | 20% |

A separate experiment was performed to measure the acceleration achieved when a low viscosity fluid (aqueous dye) replaces a high viscosity fluid (PDMS) in the flow constriction region. In this experiment, the microchannel was initially filled with the aqueous dye solution. Remaining solution in the inlet port was aspirated and liquid PDMS (2-3 μL) was introduced in the bottom of the port. Additional aqueous dye solution was pipetted onto the inlet port. The vacuum was increased to approximately −30 kPa to draw the full length of the PDMS plug through the flow constriction region in a reasonable time. When the PDMS began to exit the flow constriction region (being replaced by the lower viscosity dye solution), the flow began to accelerate slightly. As the PDMS completely exited the constriction region, the flow accelerated dramatically. The flow velocities and accelerations were varied in separate experiments by changing the strength of the vacuum.

Figure 9B:
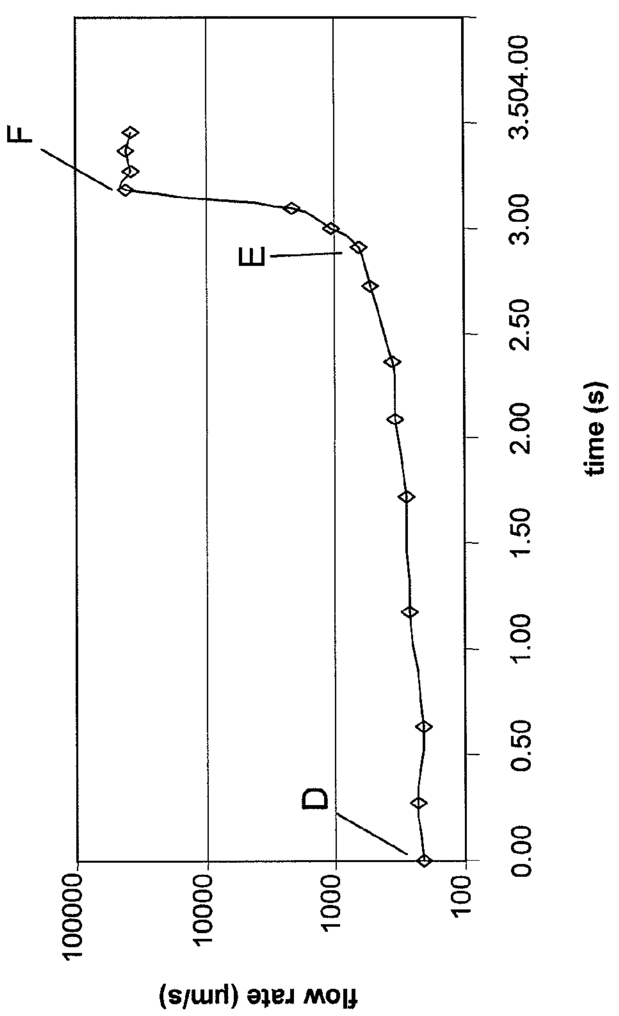

As shown in FIG. 9B and Table 1B, the linear velocity of the plugs and the flow rate increased by a factor 174 (e.g., from 236 nm/s to 41,112 μm/s, and 44 mL/s to 7729 mL/s) in 3 seconds. This is an acceleration in linear velocity of 13,229 $\mu m/s^2$, as measured by taking the absolute difference between the flow rate at a first time point just prior to the high-viscosity fluid exiting the fluid constriction region (236 nm/s, point D) and a flow rate at a second time point when the high-viscosity fluid has completely exited the flow constriction region (41,112 nm/s, point F). In this experiment, the second time point is also when the fluid has a substantially constant flow rate after exiting the flow constriction region. These differences in flow rate were divided by the amount of time between the first and second time points (3 s). Calculated as a percentage of the flow at 3 seconds, this corresponds to an acceleration (in velocity and flow rate) of 99%, or acceleration of 33%/s. The rates of acceleration can be increased by decreasing the length/volume of the high-viscosity fluid. This experiment shows that flow rate increases substantially once a relatively high-viscosity fluid exits a fluid constriction region, as illustrated by the sharp curve between points E and F in FIG. 9B.

TABLE 1B

Acceleration of fluids from a flow constriction region to a non-constriction region

| reference time (s) | V (μm/s) | dV/dt ($\mu m/s^2$) | Q (nL/s) | dQ ($nL/s^2$) | Ratio (fast:slow flow) | Acc. (%) | Acc. (%/s) |
|---|---|---|---|---|---|---|---|
| 0 | 236 | | 44 | | | | |
| 1 | 262 | 26 | 49 | 4.9 | 1.1 | 10% | 10% |
| 2 | 341 | 52 | 64 | 9.9 | 1.4 | 31% | 15% |
| 2.91 | 2,099 | 640 | 395 | 120 | 8.9 | 89% | 30% |
| 3 | 41,113 | 13,625 | 7,729 | 2,562 | 174.1 | 99% | 33% |

This example shows that flow rate can be regulated using relatively viscous fluids and flow constriction regions in a microfluidic system. This example also shows that high rates of deceleration and acceleration of fluids can be achieved.

EXAMPLE 3

Regulating Flow Rate Using Differential Viscosity of Fluids and a Flow Constriction Positioned Near an Outlet of a Microchannel System This example describes a method for regulating the flow rate in a channel using a flow constriction positioned downstream of an analysis region near an outlet of the microchannel system.

A microfluidic device having four sections, as shown in FIG. 6A, was formed using the method described in Example 1. The first section included a channel 78 having a width of 120 μm and a depth of 50 μm connecting the inlet of the device to a second section, a liquid containment region 80. Some areas of channel 7 were modified with biochemical probes to perform a heterogeneous assay (e.g., an immunoassay). The liquid containment region (33 mm in diameter, 370 μm deep) contained an absorbent material (polyester/cellulose wiper, VWR). Downstream of the chamber was a third section, a flow constriction region 82 in the form of a narrow channel (50 μm wide, 33 μm deep), which connected the liquid containment region to channel portion 84, an overflow region (Section 4, 120 μm wide and 50 μm deep).

A section of polyethylene tubing (PE-100, 0.034"×0.06" from Braintree Scientific, Inc.) was connected to a Hamilton glass syringe (VWR), to aspirate a pre-formed sequence of fluids by manually actuating the piston. The sequence included multiple pairs of plugs of PFD (5-10 μL) and red dye in PBS/Tween (5-10 μL). The total volume of the plugs was larger than the absorbent capacity of the liquid containment region. The tubing containing the reagents was fitted at the inlet of the microchannel system; another tubing connected the outlet of the system to a source of vacuum.

Figure 10:
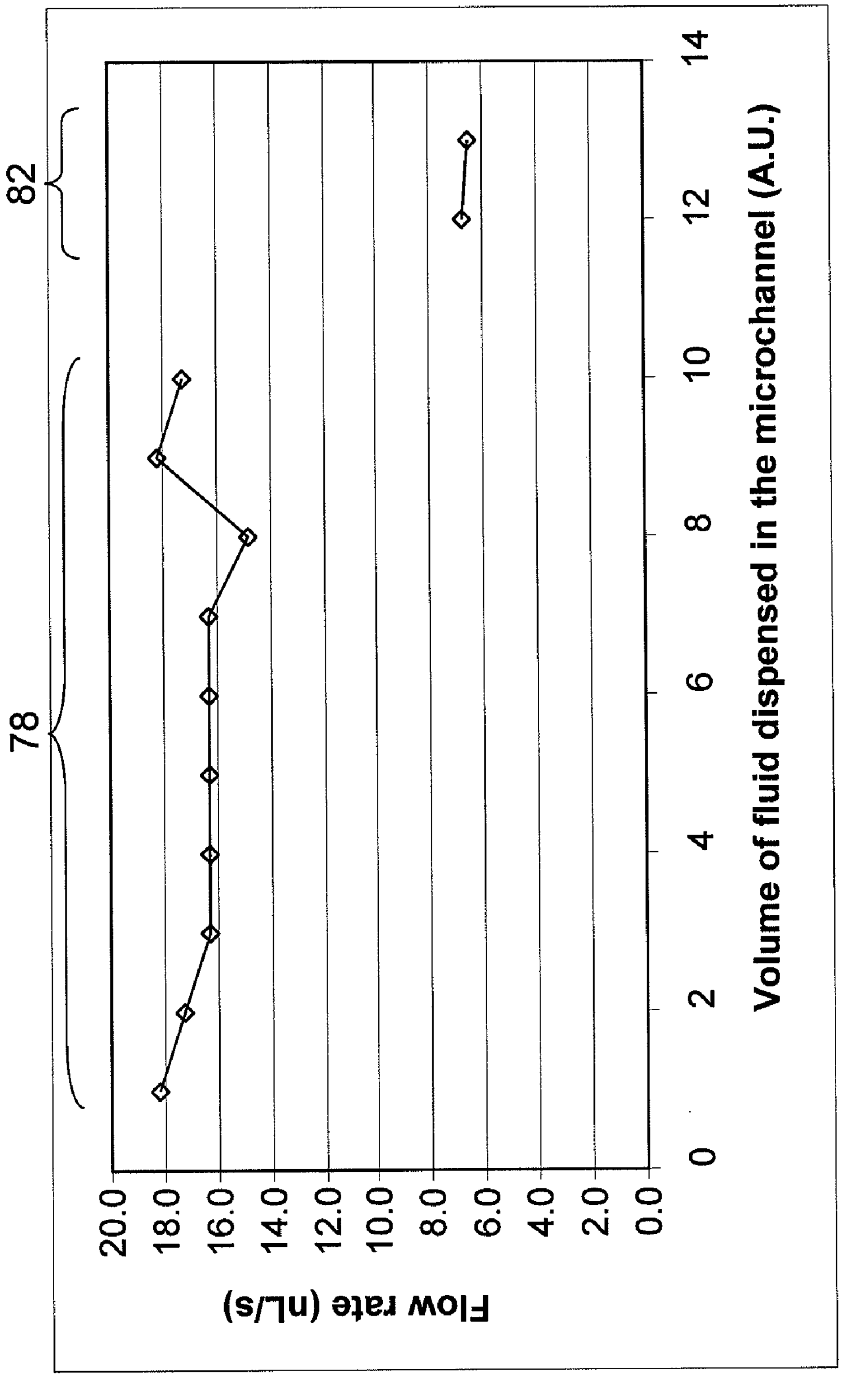
FIG. 10 shows a plot of flow rate as a function of volume of fluid dispensed in a microfluidic system having a flow constriction region positioned downstream of an analysis region according to one embodiment of the invention.

Upon activation of the vacuum (−30 kPa), the sequence of fluids moved toward the vacuum, and the fluids were trapped in the liquid containment region until the capacity of the absorbent was reached. The flow rate of the fluid was measured by recording the linear velocity of the interfaces PFD/red dye in channel 78. After the liquid containment region reached its capacity, some fluid from the liquid containment region flowed into flow constriction region 82, which caused the flow to slow down by a factor 2.5, as shown in FIG. 10. After the reduction in flow rate, the fluid took a few minutes to reach the end of the flow constriction region and fill the overflow region. This design offers a means to significantly increase the time required for the fluid to exit a liquid containment region, reach the outlet of the microfluidic system, and potentially reach the vacuum. This feature is especially useful for bioassays involving (bio-) hazardous liquid (e.g., blood) to avoid contamination of the instrumentation and/or the user in case of improper use of the microfluidic device (e.g., by applying too much liquid compared to the capacity of the waste absorbent pad).

EXAMPLE 4

Substantially Reducing Flow Rate in a Microfluidic System Using Differential Viscosity of Fluids This example describes a method for substantially reducing the flow rate of a fluid in a microchannel without the use of active valves.

A microfluidic device having a configuration similar to the one shown in FIG. 4 was formed by injection molding in polystyrene. The microfluidic device included a single section (width of 120 μm and a depth of 50 μm) in fluid communication with the inlet of the device to the outlet (vacuum). Some areas of the channel (e.g., the analysis regions) were modified with biochemical probes to perform a heterogeneous assay (e.g., an immunoassay).

A section of polyethylene tubing (PE-100, 0.034"×0.06" from Braintree Scientific, Inc.) was connected to a Hamilton glass syringe (VWR), which was used to aspirate a pre-formed sequence of fluids by manually actuating the piston. The sequence included a first reagent plug (e.g., a substrate for an enzyme) followed by a second plug of immiscible fluid having a viscosity substantially larger than that of the first liquid, for example using PFD (a viscosity of approximately 1 mPa·s) and glycerol (a viscosity of approximately 934 mPa·s), respectively. The tubing containing the reagents was connected to the inlet of the microchannel; another tubing connected the outlet to a source of vacuum.

Upon activation of the vacuum (−30 kPa), the sequence of fluids moved toward the vacuum and the PFD filled the microchannel. Once the glycerol entered the microchannel and filled about 25% of the length of the microchannel (or a length of about 20 mm), the flow rate of the fluids substantially decreased. At this point, the inlet and outlet were vented (e.g., to atmospheric pressure) and the direct observation of the PFD/glycerol interface with a stereomicroscope allowed detection of flow in the channel. The microfluidic system was then turned 90 degrees (such that the vector of gravity was parallel to the length of the channel, resulting in the apparition of hydrostatic pressure within the microfluidic device). No flow was recorded within minutes after stopping the vacuum. In a control experiment where glycerol was exchanged by red dye in PBS/Tween (which has a viscosity similar to that of the PFD), the interface was recorded to move at about 40 μm/s when the microfluidic device was tilted 90 degrees.

After disconnecting the primary driver of flow, residual flow can often still occur, such as flow induced by gravity (hydrostatic pressure). This experiment shows that the use of a high viscosity fluid in combination with a flow constriction can effectively suppress or reduce residual flow.

EXAMPLE 5

Performing a Bioassay by Modulating Flows Using Differential Viscosity of Fluids This example describes a method of performing a bioassay using fluid flows that were modified by differential viscosity of the fluids.

A microfluidic system having a configuration similar to the one shown in FIG. 4, with microchannels having a width of 120 μm and a depth of 50 μm, was formed by injection molding in polystyrene. The microfluidic system was composed of sections where the channel was linear and other sections where the channel formed a meandering region. The microchannel was continuous and did not include any intersections with other channels. The microchannel formed a series of four connected, meandering regions that served as analysis regions: analysis region 61 (zone 1), analysis region 63 (zone 2), analysis region 65 (zone 3), and analysis region 67 (zone 4) as illustrated in FIG. 4. The surface of each analysis region was modified with proteins, each protein having a specific role in the bioassay. In this example, analysis regions 61, 63, and 67 were coated with a solution of BSA (1% in PBS), whereas analysis region 65 was coated with a solution of horseradish peroxidase-labeled anti-mouse IgG in PBS (Sigma). After incubation, the surface of the microfluidic device was rinsed with PBS, DI water, and then dried with pressurized nitrogen. An adhesive lid was positioned onto the device to close off the channels. A blocking solution was then aspirated inside the channel to further coat all inner surfaces of the microchannels with BSA.

A section of polyethylene tubing (PE-100) was loaded with either a substrate solution (TMB, ready to use solution, Sigma) which was used as a control, or with a sequence of the substrate solution followed by a plug of high viscosity oil (PDMS, 100 mPa·s, Flucka). Each tubing was connected to the inlets of the microfluidic devices, and a −20 kPa vacuum was applied at the outlet to allow the liquid to flow inside the microchannels. Based on observations with a stereomicroscope, the vacuum was stopped (i.e., the device vented) when the oil reached the end of the first analysis region. Alternatively, the arrival of oil in the first analysis region could be monitored using an optical setup to measure optical density in the analysis region (e.g., using a plate reader, a drop in optical density of about 0.045 A.U. can be observed when the oil enters the analysis region). At that point, the microfluidic device was inserted inside a plate reader, which was pre-programmed to perform time-course reading of optical density in each of the analysis regions.

Once the substrate reached analysis region 65, it was hydrolyzed to produce a dye that can be used to perform a wide range of calorimetric assays. Other types of substrates could be used for fluorescence of chemiluminescence detection. In the control system, while the flow was maintained, the dye washed away as it was enzymatically produced. When the device was vented, however, the flow rate reduced and the dye accumulated within the volume of fluid in the meandering region to build up a signal. If a residual flow remained, it slowly washed away the dye, preventing the build up of a signal. Moreover, the dye carried over into neighboring analysis regions and induced false readouts. In this experiment, the devices were maintained at a horizontal position to minimize the effect of the gravity on the fluid contained in the device (i.e., hydrostatic pressures). For instance, the plate reader (where the device was positioned to perform time-course measurement) was leveled.

Figure 11A:
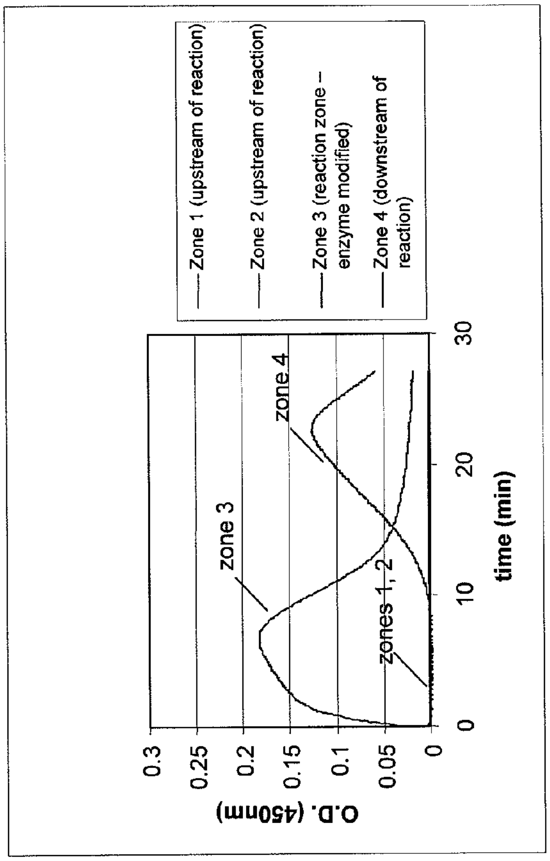
FIGS. 11A and 11B show time course measurements of reactions taking place in analysis regions positioned in series in a microfluidic system according to one embodiment of the invention.
Figure 11B:
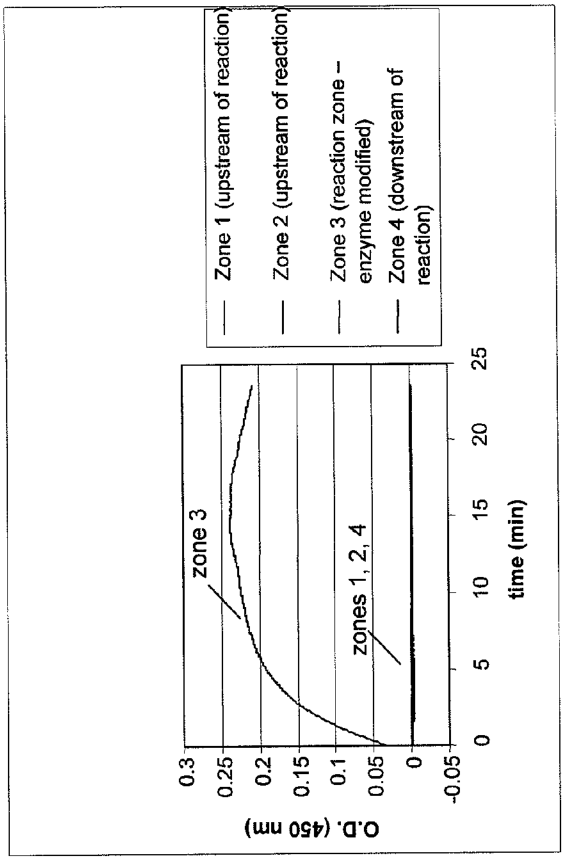

In the control device that did not contain a high viscosity fluid, it was observed that the dye from analysis region 65 (zone 3) was washed away towards the fourth analysis region (zone 4), thereby creating a significant signal in this region (FIG. 11A). In contrast, in the device containing the high viscosity fluid, a high-intensity signal remained in analysis region 65 (zone 3) only, as expected, and no dye could be detected in neighboring analysis regions (FIG. 11B). The system containing the high viscosity fluid did not promote contamination of dye to the other analysis regions because the high viscosity fluid caused a substantial reduction in flow rate and residual flow of the fluids when the source of vacuum was removed. The absence of residual flow in the device with high viscosity fluid was further demonstrated by the gain in signal intensity achieved in analysis region 65 (zone 3) compared to the device that did not have any high viscosity fluid.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:

flowing a first fluid from a first channel portion to a second channel portion in a microfluidic system, wherein a fluid path defined by the first channel portion has a larger cross-sectional area than a cross-sectional area of a fluid path defined by the second channel portion;

flowing a second fluid in a third channel portion in the microfluidic system in fluid communication with the first and second channel portions, wherein the viscosity of the first fluid is different than the viscosity of the second fluid, and wherein the first and second fluids are substantially incompressible;

without stopping the first or second fluids, causing a volumetric flow rate of the first and second fluids to decrease by a factor of at least 3 in the microfluidic system as a result of the first fluid flowing from the first channel portion to the second channel portion, compared to the absence of flowing the first fluid from the first channel portion to the second channel portion, wherein the volumetric flow rate of the first and second fluids is determined by Poiseuille's law; and effecting a chemical and/or biological interaction involving a component of the first or second fluids at a first analysis region in fluid communication with the channel portions while the first and second fluids are flowing at the decreased flow rate.

2. A method as in claim 1, wherein the first and second fluids are positioned immediately adjacent to one another.

3. A method as in claim 1, wherein the first and second fluids are separated by a third fluid.

4. A method as in claim 3, wherein the third fluid is compressible.

5. A method as in claim 1, wherein the first analysis region is a part of the second channel portion.

6. A method as in claim 1, wherein the first analysis region is a part of the third channel portion.

7. A method as in claim 1, wherein the first fluid comprises the component, and the method comprises effecting a chemical and/or biological interaction involving the component of the first fluid at the first analysis region.

8. A method as in claim 1, wherein the second fluid comprises the component, and the method comprises effecting a chemical and/or biological interaction involving the component of the second fluid at the first analysis region.

9. A method as in claim 1, wherein the first fluid has a higher viscosity than the second fluid.

10. A method as in claim 1, wherein the second fluid has a higher viscosity than the first fluid.

11. A method as in claim 1, wherein the viscosities of the first and second fluids differ by at least a factor of 40.

12. A method as in claim 1, wherein a cross-sectional area of the fluid path defined by the third channel portion is the same as the cross-sectional area of the fluid path defined by the second channel portion.

13. A method as in claim 1, wherein a cross-sectional area of the fluid path defined by the third channel portion is greater than the cross-sectional area of the fluid path defined by the second channel portion.

14. A method as in claim 1, wherein the second channel portion is positioned upstream of the first analysis region.

15. A method as in claim 1, comprising allowing the interaction involving the component to occur at least 3 times longer in the first analysis region as a result of the first fluid flowing from the first channel portion to the second channel portion, compared to the absence of the flowing of the first or second fluids from the first channel portion to the second channel portion.

16. A method as in claim 15, comprising allowing the interaction involving the component to occur for at least 60 seconds in the first analysis region.

17. A method as in claim 1, wherein the volumetric flow rate decreases at a rate of at least 3%/s as a result of the first fluid flowing from the first channel portion to the second channel portion, as measured by taking the difference between the flow rate at a first time point just prior to the first fluid entering the second channel portion, and the flow rate at a second time point when the flow rate has decreased by at least 90% while the first fluid is flowing in the second channel portion, and dividing the difference in the flow rates by the amount of time between the first and second time points.

18. A method as in claim 1, wherein the volumetric flow rate decreases by 90% in less than 3 seconds as a result of the first fluid flowing from the first channel portion to the second channel portion.

19. A method as in claim 1, wherein the volumetric flow rate of the first and/or second fluids decreases by a factor of at least 40 in the first analysis region as a result of the first fluid flowing from the first channel portion to the second channel portion.

20. A method as in claim 1, comprising applying a substantially constant, non-zero pressure drop across an inlet and an outlet of the microfluidic system.

21. A method as in claim 1, further comprising causing the volumetric flow rate of the first fluid to increase as a result of the first fluid flowing out of the second channel portion.

22. A method as in claim 1, wherein the second channel portion has a length of at least 1 cm.

23. A method as in claim 1, wherein the component is a cell.

24. A method as in claim 1, wherein the component is part of an enzyme-linked immunosorbent assay.

25. A method as in claim 1, where in the microfluidic system does not include a bypass channel connected to the first and second channel portions.

26. A method as in claim 1, wherein the microfluidic system includes no greater than 1 channel intersection.

27. A method as in claim 1, wherein the microfluidic system does not include any channel intersections.

28. A method as in claim 1, wherein flowing does not take place predominately by capillary forces.

29. A method as in claim 1, wherein the volumetric flow rates of the fluids are not controlled by an actuating valve.

30. A method as in claim 1, comprising determining a product of a chemical and/or biological reaction involving the component at the first analysis region while the first and/or second fluid is flowing.

31. A method as in claim 1, wherein the chemical and/or biological interaction involves interacting the component of the first or second fluids with a second component disposed on a surface of the first analysis region.

32. A method as in claim 1, further comprising flowing a fluid across the first analysis region at the first flow rate after the effecting step.

33. A method as in claim 1, wherein the first channel portion has a larger width than the width of the second channel portion.

34. A method as in claim 1, wherein the first channel portion has a larger width and height than the width and height of the second channel portion.

35. A method as in claim 1, wherein the cross section of at least one channel portion resembles a trapezoid.

* * * * *